(12) United States Patent
Rheinstadter et al.

(10) Patent No.: US 11,577,248 B2
(45) Date of Patent: Feb. 14, 2023

(54) BIOLOGICAL MEMBRANE-BASED SENSOR

(71) Applicant: McMaster University, Hamilton (CA)

(72) Inventors: Maikel Rheinstadter, Hamilton (CA); Sebastian Himbert, Hamilton (CA); Richard Alsop, Toronto (CA); Jose Moran-Mirabal, Dundas (CA); Sokunthearath Saem, Aurora (CA); Dawn Bowdish, Dundas (CA)

(73) Assignee: McMaster University, Hamilton (CA)

( * ) Notice: Subject to any disclaimer, the term of this patent is extended or adjusted under 35 U.S.C. 154(b) by 865 days.

(21) Appl. No.: 16/229,487

(22) Filed: Dec. 21, 2018

(65) Prior Publication Data

US 2019/0195867 A1 Jun. 27, 2019

Related U.S. Application Data

(60) Provisional application No. 62/608,680, filed on Dec. 21, 2017.

(51) Int. Cl.
*B01L 3/00* (2006.01)
*G01N 33/53* (2006.01)
(Continued)

(52) U.S. Cl.
CPC ....... *B01L 3/5085* (2013.01); *B01L 3/502715* (2013.01); *G01N 27/3272* (2013.01);
(Continued)

(58) Field of Classification Search
CPC ............. B01L 3/5085; B01L 3/502715; B01L 2300/0829; B01L 2300/0825;
(Continued)

(56) References Cited

U.S. PATENT DOCUMENTS 6,019,998 A * 2/2000 Nomoto ............... A61K 9/1271
264/4.32
7,407,768 B2 * 8/2008 Yamazaki ............... C12Q 1/18
435/287.2
(Continued)

FOREIGN PATENT DOCUMENTS

EP 2746772 B1 * 3/2016 ......... G01N 33/5432
WO WO-9823948 A1 * 6/1998 .......... B01J 19/0046

OTHER PUBLICATIONS

Schneggenburger PE, Beerlink A, Worbs B, Salditt T, Diederichsen U. A novel heavy-atom label for side-specific peptide iodination: synthesis, membrane incorporation and X-ray reflectivity. Chemphyschem. Jul. 13, 2009;10(9-10):1567-76. doi: 10.1002/cphc. 200900241. PMID: 19565579. (Year: 2009).*
(Continued)

*Primary Examiner* — Christopher L Chin
(74) *Attorney, Agent, or Firm* — Tony Orsi; Bereskin & Parr LLP / S.E.N.C.R.L, s.r.l.

(57) ABSTRACT

A biosensor detector device is disclosed suitable for use in measuring membrane fluidity or membrane permeability. The biosensor detector device is formed of a solid substrate having a lipid bilayer compatible surface, a multi-lamellar lipid membrane structure derived from a biological cell and localized on the lipid bilayer compatible surface, an aqueous layer interposed between each lipid bilayer of the multi-lamellar lipid membrane structure. The biological membrane is derived from human red blood cells and localized on the lipid bilayer compatible surface. An electrode forming all or part of the lipid bilayer compatible surface may be used to detect disruptions in the multi-lamellar lipid membrane structure and hemolytic activity in a test sample.

22 Claims, 20 Drawing Sheets

Figure 1:
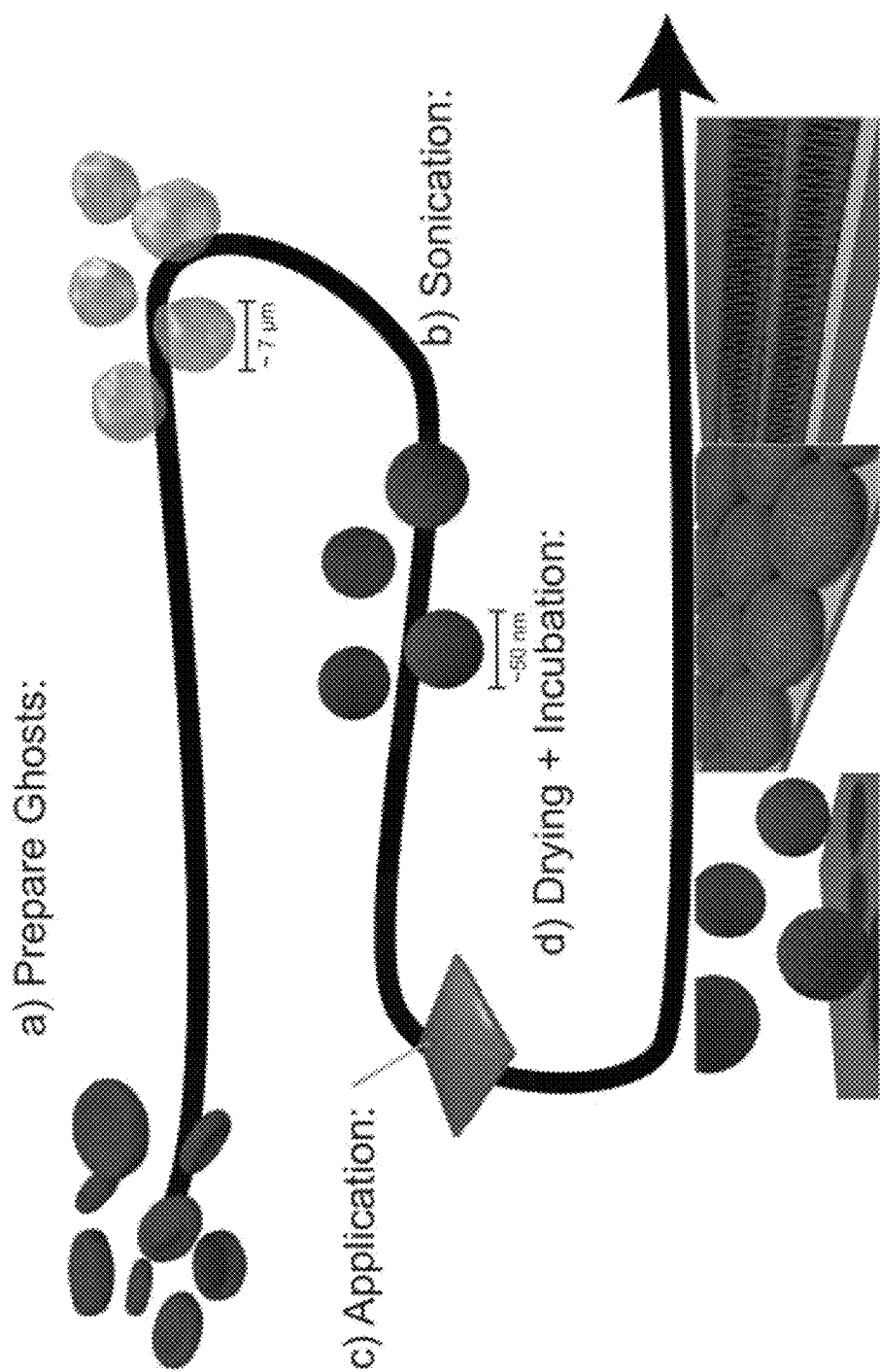

(51) Int. Cl.
  *G01N 27/327* (2006.01)
  *G01N 33/49* (2006.01)
(52) U.S. Cl.
  CPC ..... *G01N 27/3275* (2013.01); *G01N 27/3277* (2013.01); *G01N 33/49* (2013.01); *G01N 33/5306* (2013.01)
(58) Field of Classification Search
  CPC ..... B01L 2300/0822; B01L 2300/0819; B01L 2300/0816; B01L 2300/161; B01J 2219/00828; G01N 27/3272; G01N 27/31; G01N 27/40; G01N 33/49; G01N 33/5306; G01N 2405/00; G01N 33/5438; G01N 33/543; G01N 27/3275; G01N 27/3277; G01N 27/327
  USPC ..... 436/522, 806, 809; 422/82.01, 502, 407, 422/553, 503; 204/403, 403.01, 403.06, 204/290.01; 435/288.4
  See application file for complete search history.

(56) References Cited

U.S. PATENT DOCUMENTS

| | | | | |
|---|---|---|---|---|
| 2003/0134433 | A1* | 7/2003 | Gabriel | G01N 33/5438 435/287.2 |
| 2011/0091864 | A1* | 4/2011 | Karlsson | G01N 27/44747 435/4 |
| 2014/0120537 | A1* | 5/2014 | Chang | G01N 1/405 435/6.11 |

OTHER PUBLICATIONS

"The Molecular Structure of Human Red Blood Cell Membranes from Highly Oriented, Solid Supported Multi-Lamellar Membranes", Scientific Reports, |7:39661|DOI:10.1038/srep39661, published Jan. 3, 2017, 1-14 (Year: 2017).*
Lichtenberger, L.M., et al., "Insight into nsaid-induced membrane alterations, pathogenesis and therapeutics: characterization of interaction of nsaids with phosphatidylcholine," BBA-Mol Cell Biol L 1821, pp. 994-1002 (2012).
Lichtenberger, L.M., et al., "Nsaid injury to the gastrointestinal tract: evidence that nsaids interact with phospholipids to weaken the hydrophobic surface barrier and induce the formation of unstable pores in membranes," J. Pharm. Pharmacol., 58, pp. 1421-1428 (2006).
Zhou, Y., et al., "Nonsteroidal anti-inflammatory drugs alter the spatiotemporal organization of ras proteins on the plasma membrane," Journal of Biological Chemistry, 287, 20, pp. 16586-16595 (2012).
Alsop, R.J., and Rheinstadter, M.C., "Lipid rafts in binary lipid/cholesterol bilayers," In Membrane Organization and Lipid Rafts in the Cell and Artificial Membranes, Cell Biology Research Progress, edited by Angel Catala, pp. 17-42, (Nov. 2016).
Alsop, R.J., et al., "Swelling of phospholipid membranes by divalent metal ions depends on the location of the ions in the bilayers," Soft Matter, 12, pp. 6737-6748, (2016B).
Kaestner, L., "Red blood cell ghosts and intact red blood cells as complementary models in photodynamic cell research," Bioelectrochemistry, 62, pp. 123-126 (2004).
Steck, T.L., "The organization of proteins in the human red blood cell membrane a review," The Journal of Cell Biology, 62, pp. 1-19 (1974).
Barrett, M.A, et al., "Interaction of aspirin (acetylsalicylic acid) with lipid membranes," PLoS ONE 7, e34357 (2012).
Mohandas, N., and Gallagher, P.G., "Red cell membrane: past, present, and future," Blood, 112, 10, pp. 3939-3948 (2008).
Watts, T.H., et al., "Antigen presentation by supported planar membranes containing affinity-purified I-Ad ," Proc. Natl. Acad. Sci. U.S.A., 81, pp. 7564-7568 (1984).
Pabst, G., et al., "Applications of neutron and x-ray scattering to the study of biologically relevant model membranes," Chemistry and Physics of Lipids, 163, pp. 460-479 (2010).
Reviakine, I., and Brisson, A., "Formation of supported phospholipid bilayers from unilamellar vesicles investigated by atomic force microscopy," Langmuir 16, pp. 1806-1815 (2000).
Nagle, J.F., and Tristram-Nagle, S., "Structure of lipid bilayers," Biochim. Biophys. Acta., 1469, pp. 159-195 (2000).
Chen, S.H., et al., "Collective dynamics in fully hydrated phospholipid bilayers studied by inelastic x-ray scattering," Phys. Rev. Lett., 86, 4, pp. 740-743 (2001).
Rheinstadter, M.C., et al., "Collective dynamics of lipid membranes studied by inelastic neutron scattering," Phys. Rev. Lett., 93, 108107 (2004).
Tanaka, M., and Sackmann, E., "Polymer-supported membranes as models of the cell surface," Nature, 437, pp. 656-663 (2005).
Daillant, J., et al., "Structure and fluctuations of a single floating lipid bilayer," Proceedings of the National Academy of Sciences of the United States of America, 102, 33, pp. 11639-11644 (2005).
Rheinstadter, M.C., et al., "Dispersion relation of lipid membrane shape fluctuations by neutron spin-echo spectrometry," Phys. Rev. Lett., 97, 048103 (2006).
Zhou, X., et al., "Supported lipid bilayer/carbon nanotube hybrids," Nature nanotechnology, 2, pp. 185-190 (2007).
Kucerka, N., et al., "Fluid phase lipid areas and bilayer thicknesses of commonly used phosphatidylcholines as a function of temperature," Biochimica et Biophysica Acta (BBA)-Biomembranes, 1808, pp. 2761-2771 (2011).
Rheinstadter, M.C., "Lipid membrane dynamics," in Dynamics of Soft Matter: Neutron Applications, edited by Sow-Hsin Chen Victoria García Sakai, Christiane Alba-Simionesco (Springer Science & Business Media, 2011) p. 263-286.
Moores, B., et al., "Effect of surfaces on amyloid fibril formation," PLoS One, 6, e25954 (2011).
Kucerka, N., et al., "Structure of fully hydrated fluid phase DMPC and DLPC lipid bilayers using x-ray scattering from oriented multilamellar arrays and from unilamellar vesicles," Biophys. J., 88, pp. 2626-2637 (2005).
Dies, H., et al., "The interaction between amyloid-β peptides and anionic lipid membranes containing cholesterol and melatonin," PLOS ONE , pp. 1-17 (2014).
Marquardt, D., et al., "Neutron scattering at the intersection of heart health science and biophysics," Journal of Cardiovascular Development and Disease, 2, pp. 125-140 (2015).
Cathcart, K., et al., "Effect of cholesterol on the structure of a five-component mitochondria-like phospholipid membrane," Membranes, 5, pp. 664-684 (2015).
Alsop, R.J., et al., "Aspirin inhibits formation of cholesterol rafts in fluid lipid membranes," Biochimica et Biophysica Acta (BBA)-Biomembranes, 1848, pp. 805-812 (2015A).
Alsop, R.J., et al., "Cholesterol expels ibuprofen from the hydrophobic membrane core and stabilizes lamellar phases in lipid membranes containing ibuprofen," Soft Matter, 11, pp. 4756-4767 (2015B).
Tang, J., et al., "Amyloid-β 25-35 peptides aggregate into cross-β sheets in unsaturated anionic lipid membranes at high peptide concentrations," Soft Matter, 12, pp. 3165-3176 (2016).
Alsop, R.J., et al., "The lipid bilayer provides a site for cortisone crystallization at high cortisone concentrations," Scientific Reports, 6, pp. 1-10 (2016A).
Welti, R., et al., "Gel-phase phospholipid in the plasma membrane of sterol-depleted mouse LM cells," The Journal of Biological Chemistry, 256, 14, pp. 7528-7535 (1981).
Jewell, S.A., et al., "Clostridium perfringens α-toxin interaction with red cells and model membranes," Soft Matter, 11, pp. 7748-7761 (2015).
Mills, T.T., et al., "Effects of cholesterol and unsaturated dopc lipid on chain packing of saturated gel-phase DPPC bilayers," Gen. Physiol. Biophys., 28, pp. 126-139 (2009).
Yang, F.C., et al., "The structure of people's hair," PeerJ, 2, e619 (2014).
Armstrong, C.L., et al., "The observation of highly ordered domains in membranes with cholesterol," PLOS ONE, 8, e66162 (2013).

(56) References Cited

OTHER PUBLICATIONS

Meinhardt, S., et al., "Monolayer curvature stabilizes nanoscale raft domains in mixed lipid bilayers," Proc. Natl. Acad. Sci. U.S.A., 110, 12, pp. 4476-4481 (2013).

Zhang, Y., et al., "Effect of shampoo, conditioner and permanent waving on the molecular structure of human hair," PeerJ, 3, e1296 (2015).

Toppozini, L., et al., "Structure of cholesterol in lipid rafts," Physical Review Letters, 113, 228101 (2014).

Neukirch, S., et al., "Chirality of coiled coils: elasticity matters," Physical Review Letters, 100, 038105 (2008).

Roth, G.J., et al., "Acetylation of prostaglandin synthase by aspirin," Proc. Natl. Acad. Sci. U.S.A., 72, 8, pp. 3073-3076 (1975).

Patrono, C., et al., "Low-dose aspirin for the prevention of atherothrombosis," N. Engl. J. Med., 353, pp. 2373-2383 (2005).

O'Donnell, V.B., et al., "Platelet lipidomics modern day perspective on lipid discovery and characterization in platelets," Circulation Research, 114, pp. 1185-1203 (2014).

Lupas, A.N., and Gruber, M., "The structure of α-helical coiled coils," Advances in Protein Chemistry, 70, pp. 37-38 (2005).

Padmavathi, P., et al., "Smoking-induced alterations in platelet membrane fluidity and Na+/K+-ATPase activity in chronic cigarette smokers," J Atheroscler Thromb., 17, 6, pp. 619-627 (2010).

Knutton, S., et al., "Low-angle x-ray diffraction and electron-microscope studies of isolated erythrocyte membranes," Journal of Cell Science 7, pp. 357-371 (1970).

Stamatoff, J.B., et al., "X-ray diffraction studies of human erythrocyte membrane structure," Proceedings of the National Academy of Sciences, 72, 2, pp. 531-534 (1975).

Minetti, G., et al., "Red cell investigations: Art and artefacts," Blood Reviews, 27, pp. 91-101 (2013).

Gratzer, W.B., "The red cell membrane and its cytoskeleton," Biochemical Journal, 198, pp. 1-8 (1981).

Lucio, M., et al., "Drug-membrane interactions: significance for medicinal chemistry," Current Medicinal Chemistry 17, pp. 1795-1809 (2010).

Richter, R., et al., "Pathways of lipid vesicle deposition on solid surfaces: A combined QCM-D and AFM study," Biophys. J., 85, 3035-3047 (2003).

Armstrong, C.L., et al., "Diffusion in single supported lipid bilayers studied by quasi-elastic neutron scattering," Soft Matter, 6, pp. 5864-5867 (2010).

Nagle, J.F., and Wiener, M.C., "Relations for lipid bilayers," Biophys. J., 55, pp. 309-313 (1989).

Tristram-Nagle, S., et al., "Structure of gel phase dmpc determined by x-ray diffraction," Biophysical Journal, 83, pp. 3324-3335 (2002).

\* cited by examiner

BIOLOGICAL MEMBRANE-BASED SENSOR

RELATED APPLICATION

The present application claims the benefit of U.S. Provisional Application Ser. No. 62/608,680 filed Dec. 21, 2017, the entire contents of which are hereby incorporated by reference.

FIELD

The present application relates to multi-lamellar lipid membranes and more specifically to multi-lamellar lipid membranes derived from biological cells and their use as a biosensor.

BACKGROUND

The presence of pale cells with no internal content in a blood smear is typically indicative of a disease. These cells are produced by hemolysis and have been named red blood cell (RBC) ghosts based on their appearance under the microscope. RBC ghosts can be prepared artificially and their preparation is a well-known protocol in biological and medical research [1-3]. The first published protocol in 1963 by Dodge, Mitchell and Hanahan describes the extraction of the cell membrane from RBCs through hemolysis and was an essential step in the development of membrane proteomics and lipidomics [4, 5]. The RBC lipid bilayer consists of equal amounts of cholesterol and phospholipids, such as phosphatidylcholine, sphingomyelin, phosphatidylethanolamine and phosphatidylserine [6].

Another well-known protocol is the preparation of highly oriented stacks of artificial supported lipid bilayers on silicon wafers [7, 8]. This technique allows the analysis of molecular structure and dynamical properties of these bilayers using biophysical techniques, such as fluorescence microscopy, atomic force microscopy, as well as X-ray and neutron scattering [8-17]. This approach has advanced significantly during the past decades and is now used to study complex, multi-component membranes and their interaction with drugs, small molecules [8, 18-27], bacteria [28, 29], and in particular lipid rafts, i.e. functional lipid domains [30-36].

Blood tests are routinely used to detect and identify infectious agents and inform therapeutic treatment. Blood agar plates are the current gold-standard tests for detecting and identifying bacteria with a hemolytic activity, i.e., bacteria which break the red blood cell (RBC) membrane. In this test, clinical swabs or specimens are spread on an agar plate (a growth medium), which typically contains 5% blood, and the plate is incubated overnight. Hemolytic activity is evaluated visually as changes to the colour of the plate and pattern formation. Typically, blood from sheep or horses is used for these tests as human blood has the potential to expose hospitals and technicians to dangerous pathogens.

SUMMARY

This application discloses the preparation of highly oriented stacks of RBC membranes on silicon wafers also referred to herein as multi-lamellar lipid membrane structures. These structures are ideally suited for the study of molecular properties of RBC membranes in-vitro using biophysical techniques and development of sensors for blood tests. Presented is the detailed preparation and characterization of the morphology of the membranes, as well as their molecular structure, and present evidence for nanometer-sized domains of peptide coiled-coils, and liquid ordered ($l_o$) and liquid disordered ($l_d$) lipid domains in RBC membranes.

To demonstrate the potential of RBC membranes on a silicon chip for the study of drug interactions, the effects of a common drug on molecular membrane structure were studied. When present in the body, aspirin (acetylsalicylic acid, ASA) and its metabolites interact with the cyclooxygenase (COX) pathway. The inhibition of both COX isoforms, COX-1 and COX-2, by higher dose aspirin is believed to lead to analgesic and anti-inflammatory effects, while lower doses, sufficient to inhibit COX-1 activity, lead to anti-platelet activity [37, 38]. There is recent evidence that membrane composition and fluidity play an important role in platelet cell function [39-41], possibly related to the formation of rafts [42].

Direct experimental evidence that aspirin incorporates into the head group region of erythrocyte membranes and leads to an increase of lipid tail distances and a decrease in membrane width, indicating increased membrane fluidity is presented. ASA preferably interacts with the head group region of $l_o$ domains of the RBC membranes.

Also described here is a proof of concept for a blood test to detect hemolytic activity. In one embodiment, the test uses an electrochemical sensor where a structured electrode is coated with human red blood cell membranes (HBLOC sensor). A droplet of blood can be applied directly on the sensor and a leak current across the red blood cell membranes is detected, which is indicative of membrane damage, such as puncture or rupture. An electronic reading proportional to the damage is available within minutes.

The HBLOC sensor has significant advantages over the currently used tests. With one droplet of blood, molecules and bacteria with hemolytic activity can be safely and easily detected within a few minutes, speeding up diagnosis and therapy. The test can be implemented in a small portable device, akin to the existing small and portable glucose meters. Thus, blood testing can be done directly at the patient's bed using a portable platform operated by doctors or paramedics. An electronic reading provides a direct, quantitative measure of hemolytic activity (alpha- or beta-hemolysis). 60% of hemolytic bacteria are known to be "culture negative", i.e., they cannot be cultivated on standard blood agar plates. The HBLOC test measures hemolytic activity without need of culturing the bacteria. The test uses real human blood instead of sheep or horse blood and will also detect those bacteria, which are known not to harm non-human cells.

This test has the potential to become a routine test in health care. This innovation is based on two key techniques: the combination of the ability to reproducibly isolate and deposit complete human red blood cell membranes on solid surfaces and to produce high surface area electrochemical sensors that can be functionalized for maximum compatibility with such membranes. This combination of biotechnology and nanotechnology resulted in natural smart sensors that detect membrane damage by dangerous bacteria.

Accordingly, in one aspect there is provided a biosensor comprising:

a solid substrate having a lipid bilayer compatible surface;

a multi-lamellar lipid membrane structure derived from a plurality of biological cells and localized on the lipid bilayer compatible surface; and an aqueous layer interposed between each lipid bilayer of the multi-lamellar lipid membrane structure.

In one embodiment, the multi-lamellar lipid membrane structure is derived from red blood cells or red blood cell ghosts, optionally from human red blood cells or red blood cell ghosts.

In one embodiment, the multi-lamellar lipid membrane structure is prepared by incubating a lipid bilayer compatible surface with a preparation of red blood cell ghosts, wherein the red blood cell ghosts anneal to form the multi-lamellar lipid membrane structure. Also provided are methods for preparing red blood cell ghosts and/or a multi-lamellar lipid membrane structure as described herein. In one embodiment, the lipid bilayer compatible surface is incubated with the preparation of red blood cell ghosts at a temperature between about 35° C. and 40° C., optionally about 37° C. in the presence of a saturated potassium sulfate solution.

In one embodiment, the lipid bilayer compatible surface comprises acid treated $SiO_2$. In one embodiment, the biosensor comprises at least one electrode. In one embodiment, the electrode comprises all or part of the lipid bilayer compatible surface. In one embodiment, the electrode is functionalized in order to render the lipid biolayer compatible surface hydrophilic. For example, in one embodiment the surface of the electrode is acid treated, treated with organic solvents, or with plasma.

In one embodiment, the biosensor further comprises a power supply and/or a detector for detecting a change in current and/or potential. In one embodiment, the biosensor comprises a microfluidic device, well, or channel for receiving a sample in contact with the lipid bilayer compatible surface.

In another aspect, there is provided a method of detecting membrane disruption activity in a sample using a multi-lamellar lipid membrane structure as described herein. In one embodiment, the method comprises:

contacting the sample with a biosensor as described herein; and detecting a change in the multi-lamellar lipid membrane structure in response to the sample.

In one embodiment, the biosensor comprises at least one electrode and detecting the change in the multi-lamellar lipid membrane structure comprises voltammetry, optionally cyclic voltammetry, chronoamperometry, differential multi pulse voltammetry, double potential pulse techniques or additive differential pulse voltammetry. In one embodiment, the sample further comprises a redox-indicator, optionally ferricyanide.

The biosensors and methods described herein may be used to detect the presence of hemolytic agents, such as hemolytic bacteria, in a sample. Accordingly, in one embodiment the sample is a biological sample from a subject, optionally a blood sample. In one embodiment, the sample is an environmental sample such as a water sample or food sample. In one embodiment, detecting membrane disruption activity in a sample is indicative of the presence of a hemolytic agent in the sample.

Also provided are kits comprising one or more biosensors as described herein. Optionally, the kits further comprises instructions for performing a method for detecting membrane disruption activity in a sample. Also provided are kits comprising reagents for preparing a biosensor as described herein.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

DRAWINGS

The embodiments of the application will now be described in greater detail with reference to the attached drawings in which:

FIG. 1. Schematic of the Blood-on-a-Chip preparation protocol. The protocol is based on the original protocol for the preparation of red blood cell ghosts (a). The RBCs are then sonicated to form small uni-lamellar vesicles and centrifuged (b) before the solution is applied to silicon wafers (c). The membranes are dried and annealed (d) to form well developed multi-lamellar stacks of red blood cell membranes supported on silicon wafers.

Figure 2:
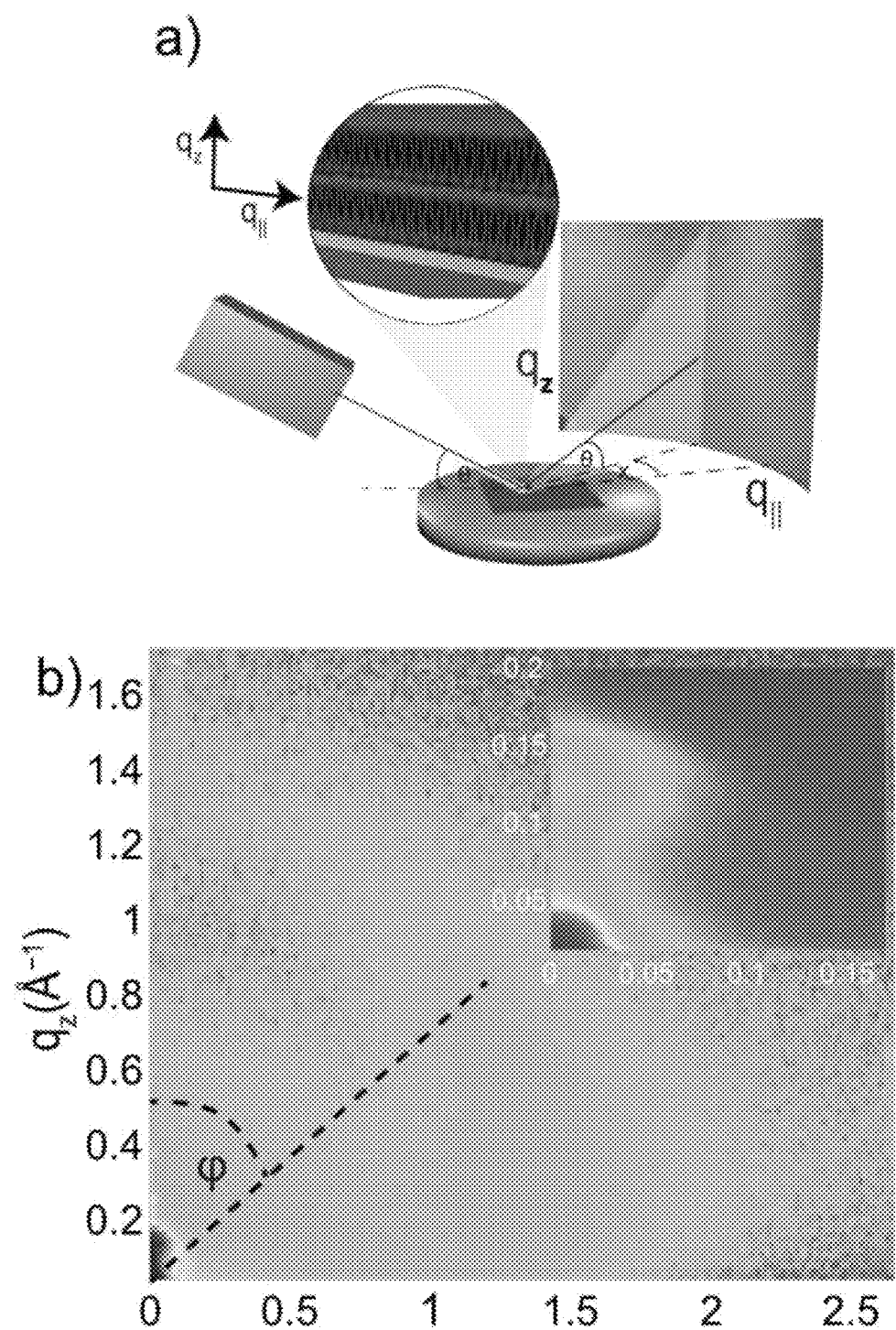
Figure 2:
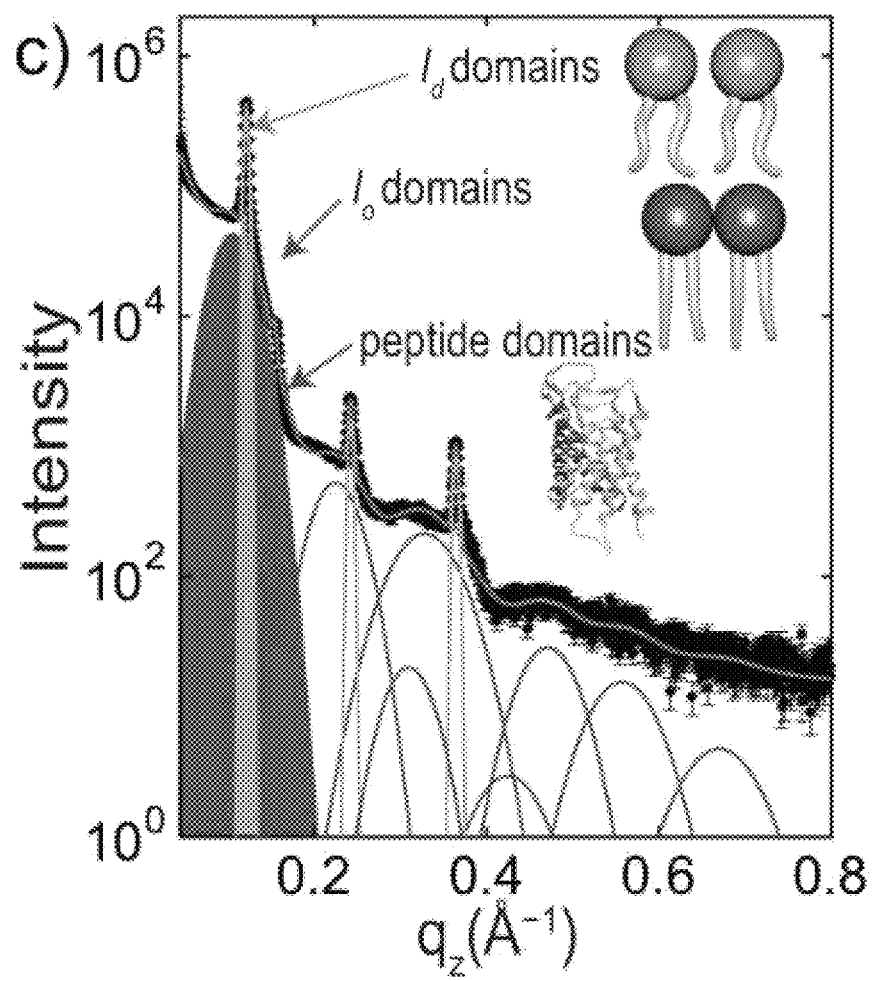
Figure 2:
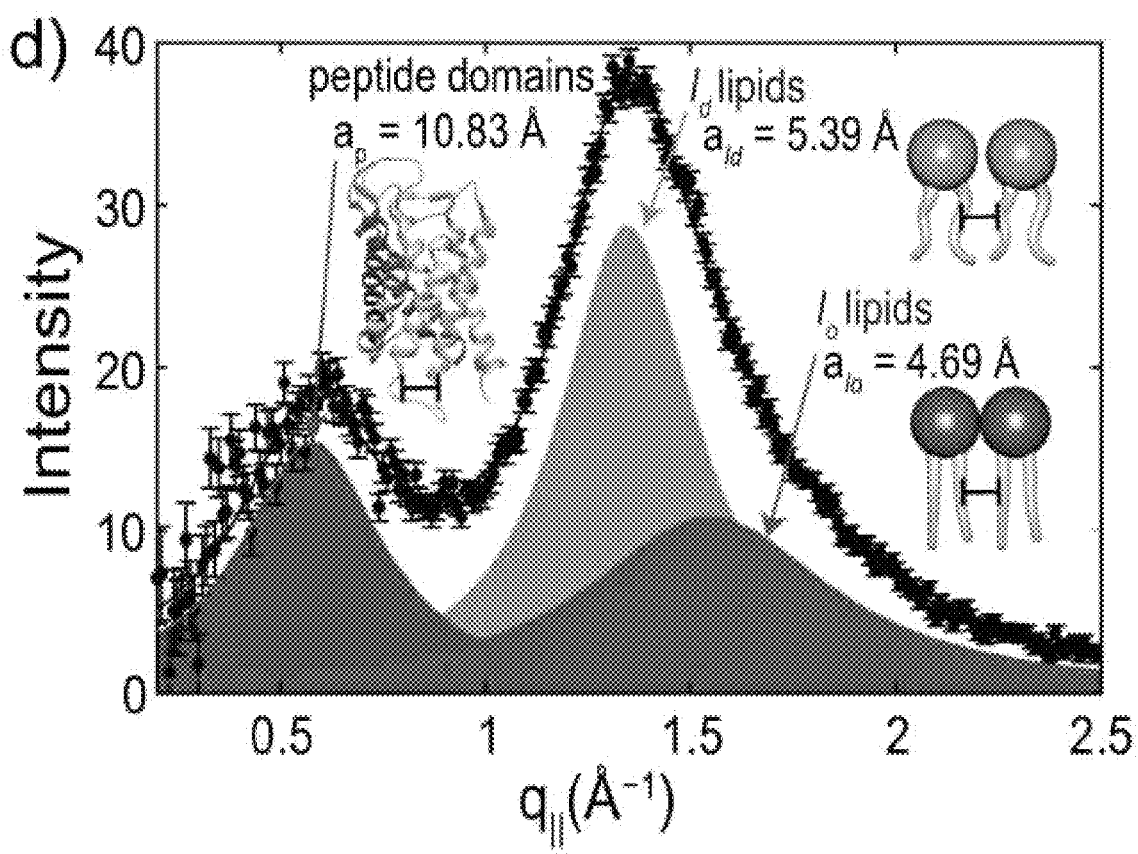

FIG. 2. Removal of hemoglobin from the erythrocyte blood fraction after induced lysis in hypotonic buffer. a) Ghost samples lose their characteristic red color through sequential centrifugation and washes. b) Comparison of UV-vis absorbance curves at different stages within ghost preparation. Characteristic hemoglobin absorbance signatures are significantly reduced in the final solution after the procedure. c) Schematic of the UV-vis setup.

Figure 3:
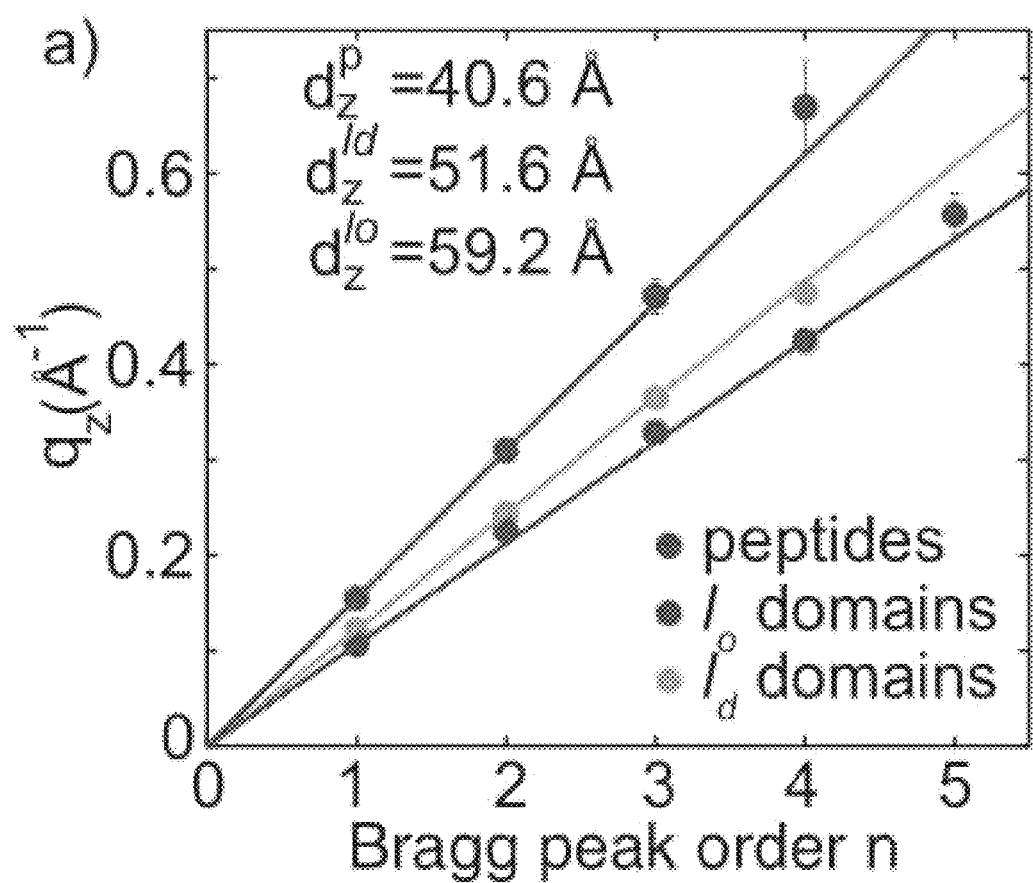
Figure 3:
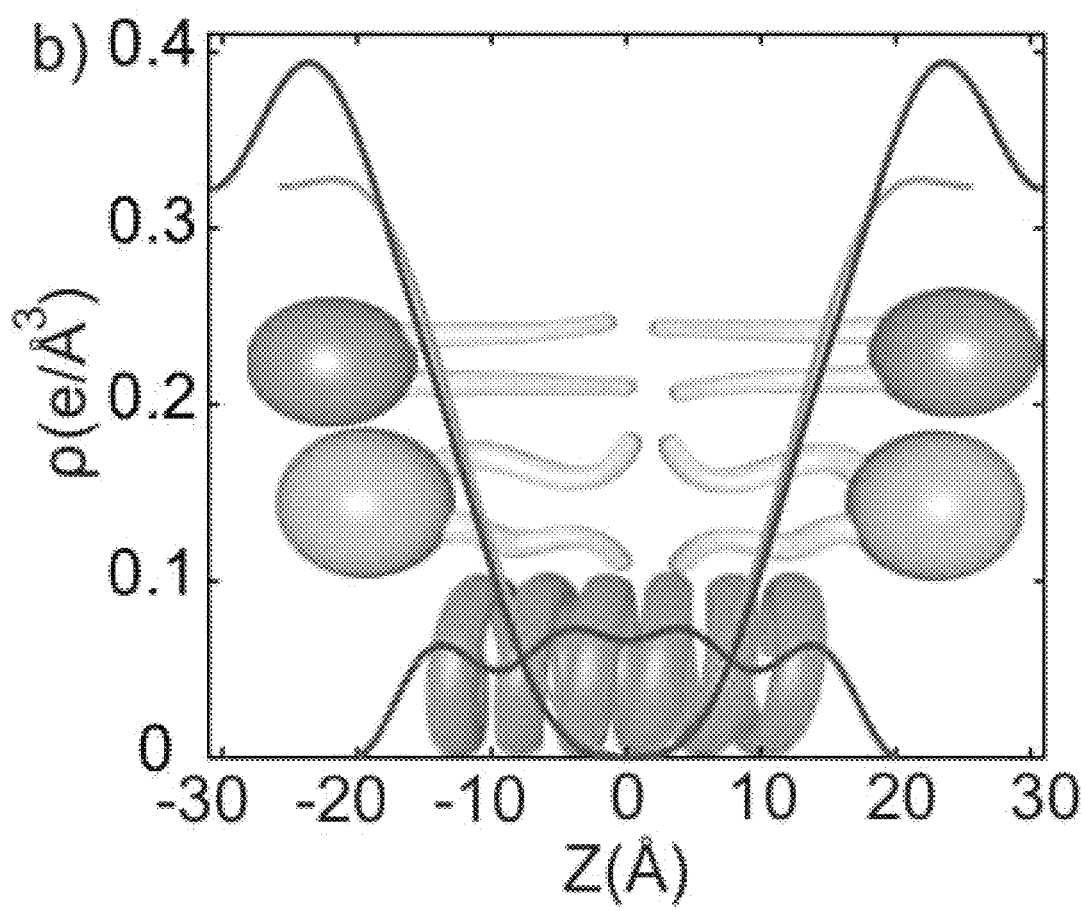
Figure 3:
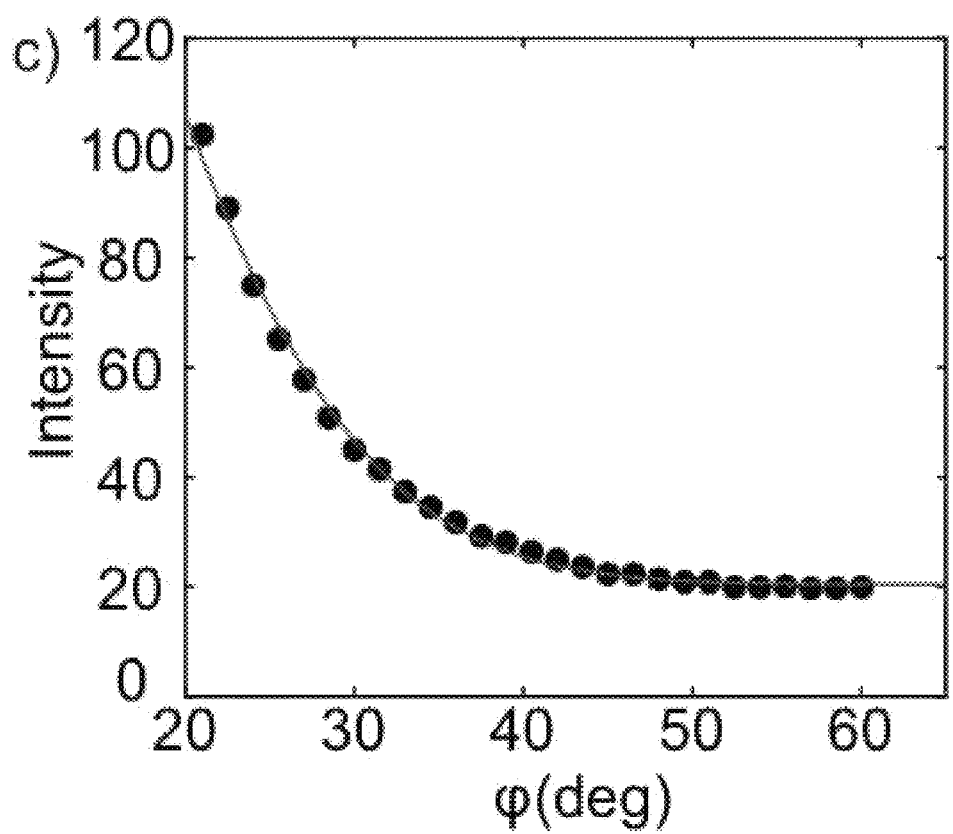

FIG. 3. Fluorescence microscopy images of the ghost solution before and after sonication. The membrane was labelled using DiI in parts a) and c), while Alexa Fluor 488 labelled phalloidin was used to label the F-actin network in b) and d). Before sonication, ghosts of highly irregular shape and a large size distribution are observed including 'ghosts inside of ghosts'. The solution also contains large clusters of actin. Small uni-lamellar vesicles are observed after sonication and no actin particles (within the resolution of the microscope used).

Figure 4:
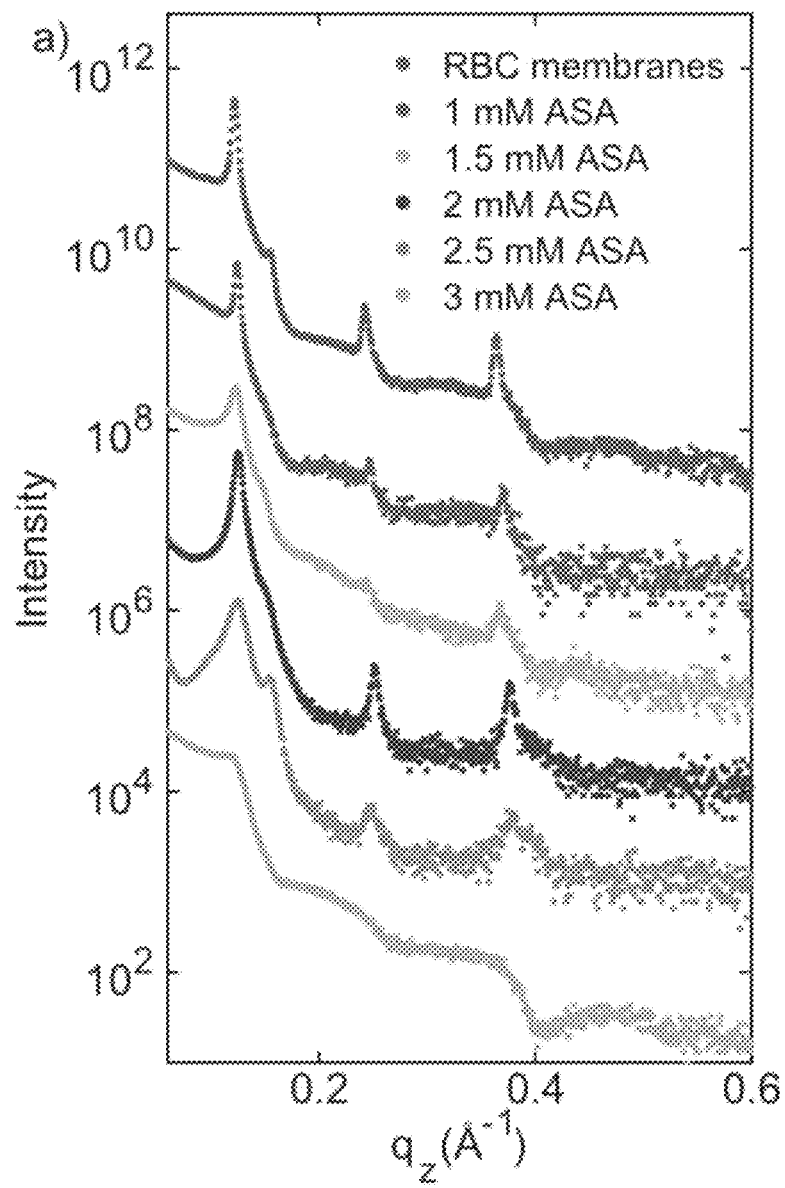
Figure 4:
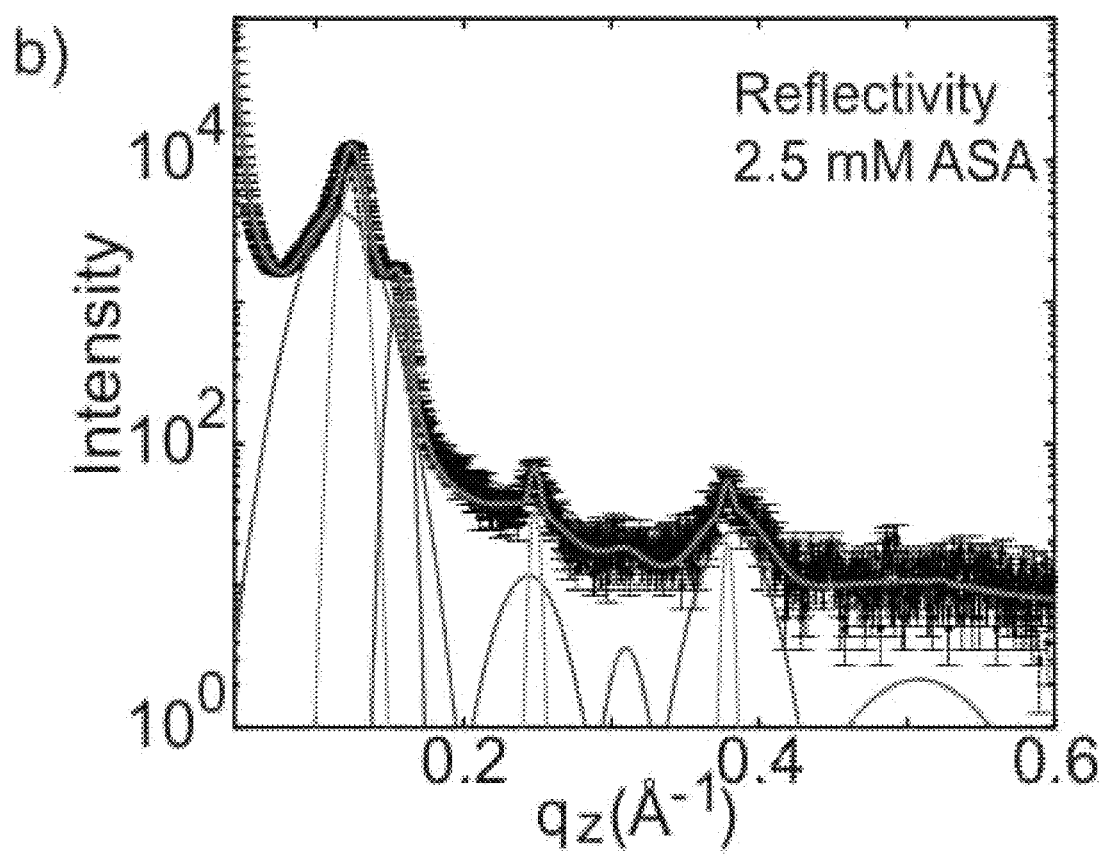
Figure 4:
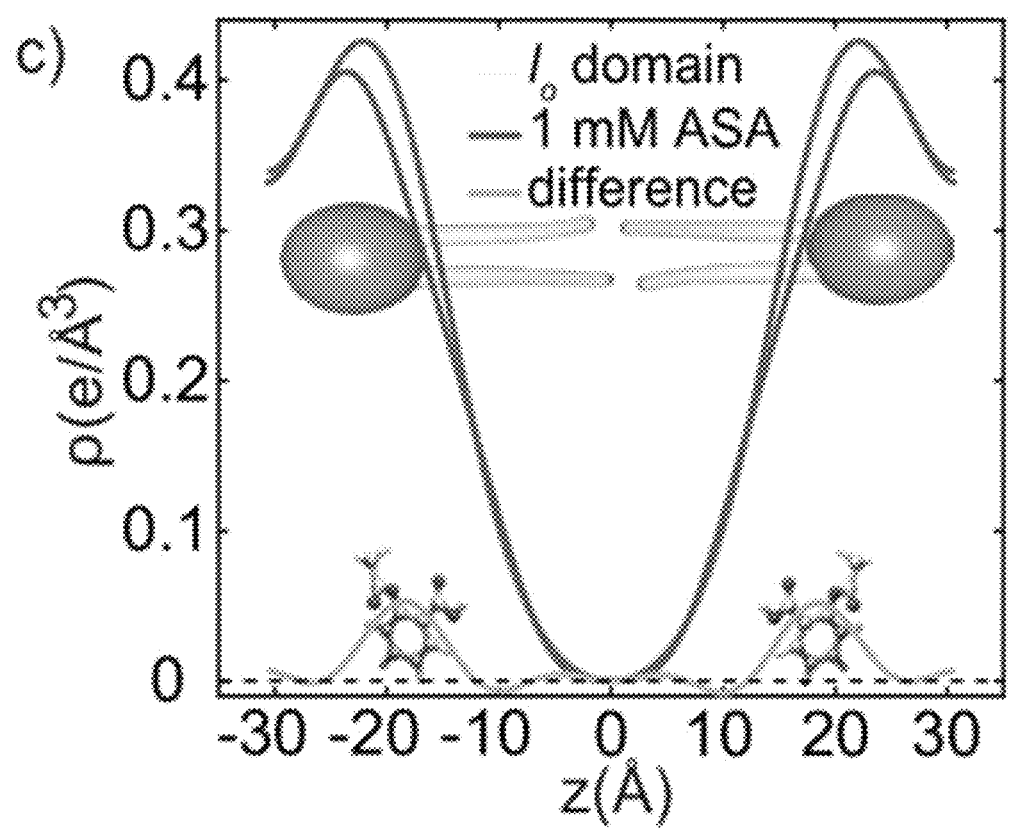
Figure 4:
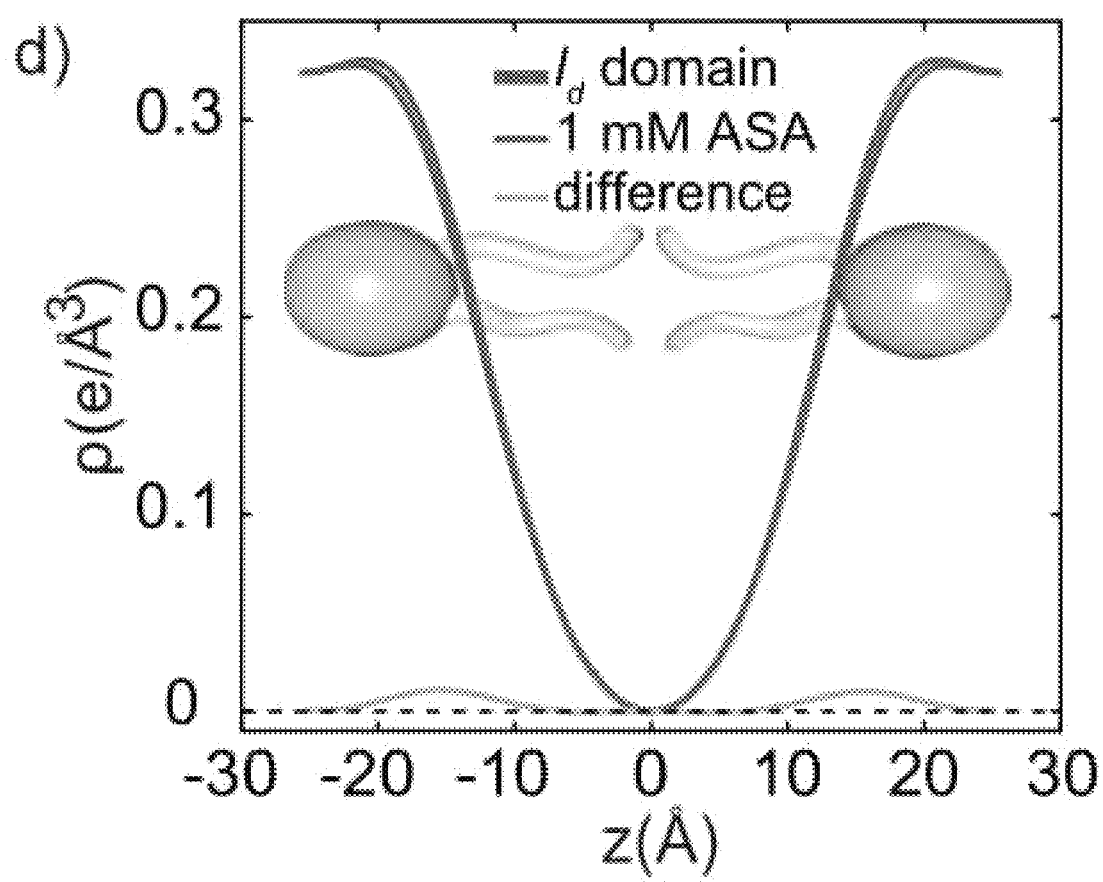
Figure 4:
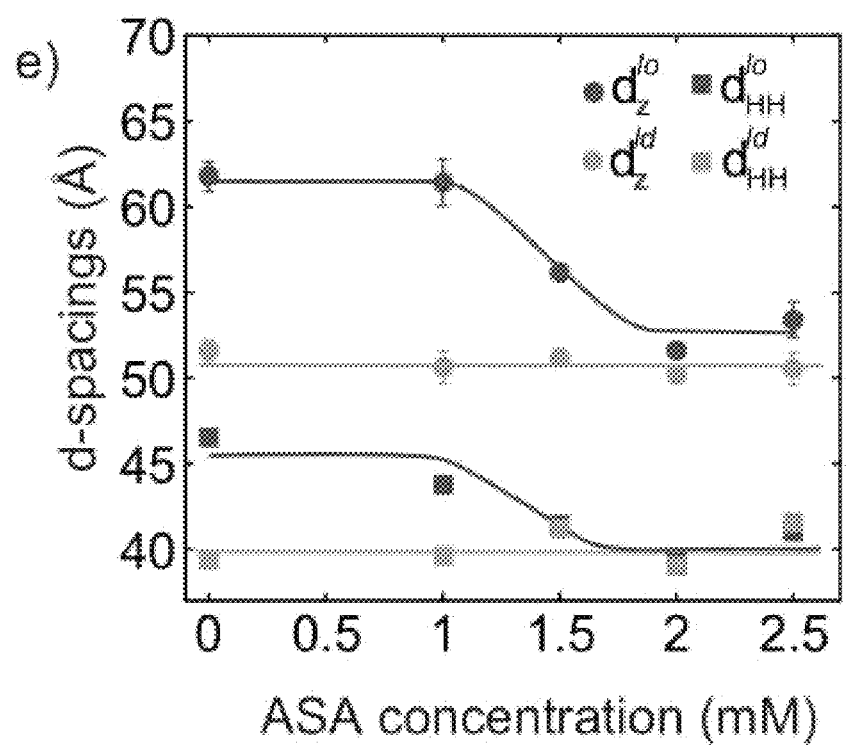

FIG. 4. Photos of the silicon chips after a) application of the RBC solution on a hydrophilic wafer and fast drying, b) application on a hydrophobic wafer after slow drying. c) and d) show hydrophilic wafers after slow drying and slow drying and annealing, respectively. See text for details.

Figure 5:
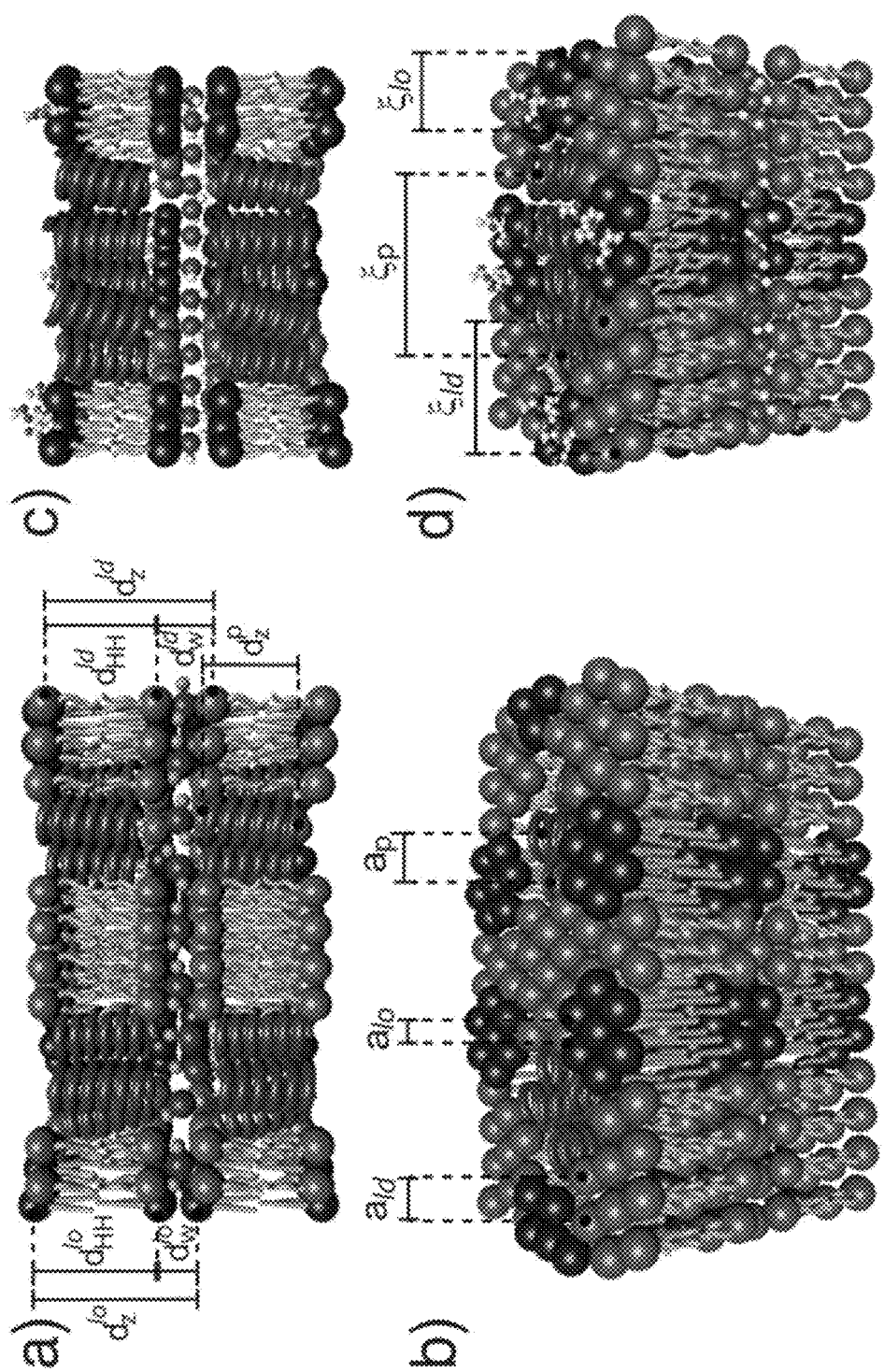

FIG. 5. Overview of the X-ray diffraction results. The setup is schematically shown in a). The highly aligned membranes are oriented on the X-ray diffractometer, such that $q_z$ measures out-of-plane, and $q_{\parallel}$ in-plane membrane structure. b) Two-dimensional data. The main features are a series of intensities along the $q_z$-axis and two broad signals along the in-plane axis $q_{\parallel}$. c) shows a cut along $q_z$. The data are well fit by three series of Bragg peaks corresponding to three different lamellar spacings assigned to $l_o$ and ld lipid domains (green and blue) and coiled-coil α-helical peptide domains (red). d) The in-plane signals show three correlation peaks corresponding to the packing of α-helices in the peptide domains (ap=10.83 Å), and packing distances of ld (ald=5.39 Å) and lo lipid tails (alo=4.69 Å) in the hydrophobic membrane core.

Figure 6:
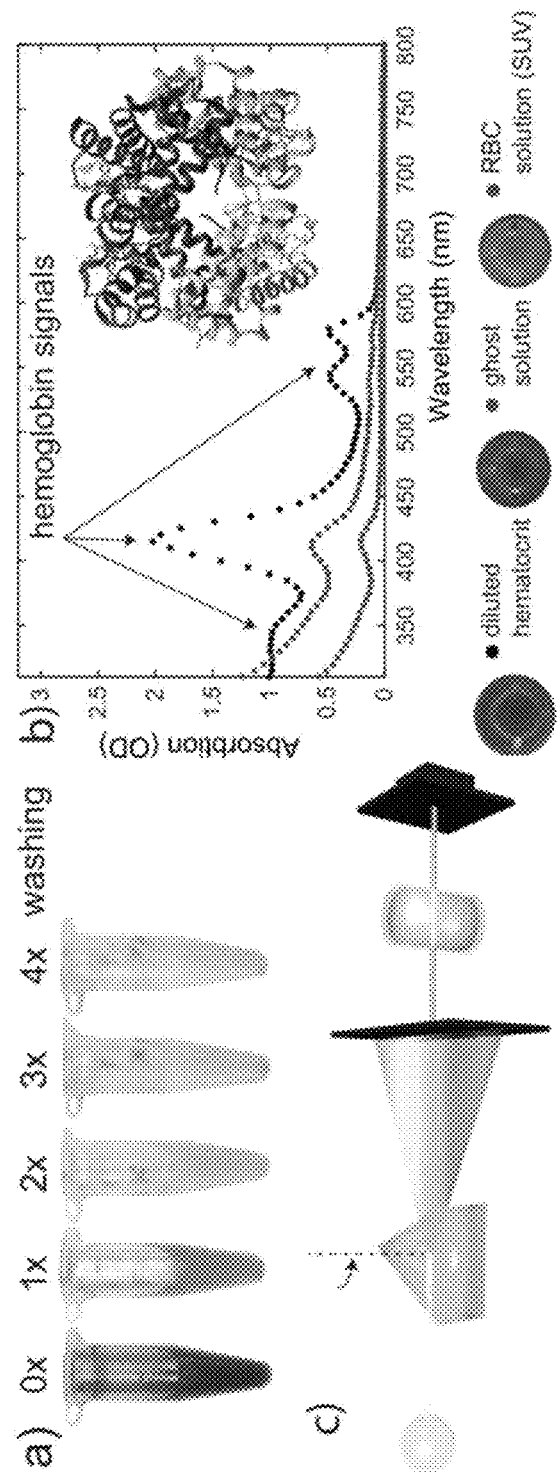

FIG. 6. Analysis of the X-ray diffraction data in FIG. 5. The lamellar spacings of the peptide, and the $l_o$ and ld lipid domains are determined from the slopes of $q_z$ vs. n plots. b) Shows the corresponding electron densities as determined through Fourier analysis of the out-of-plane diffraction data. The densities for the $l_o$ and ld lipid domains agree well with literature values. The peptide domain shows an almost constant density in the hydrophobic membrane core, indicative of trans-membrane peptide domains. c) Membrane orientation is determined from radial integration of the scattered intensity along the meridional degree, ϕ. The solid line is a fit using a Gaussian profile. RBC membranes are 90.9% oriented with respect to the silicon substrate.

Figure 7:
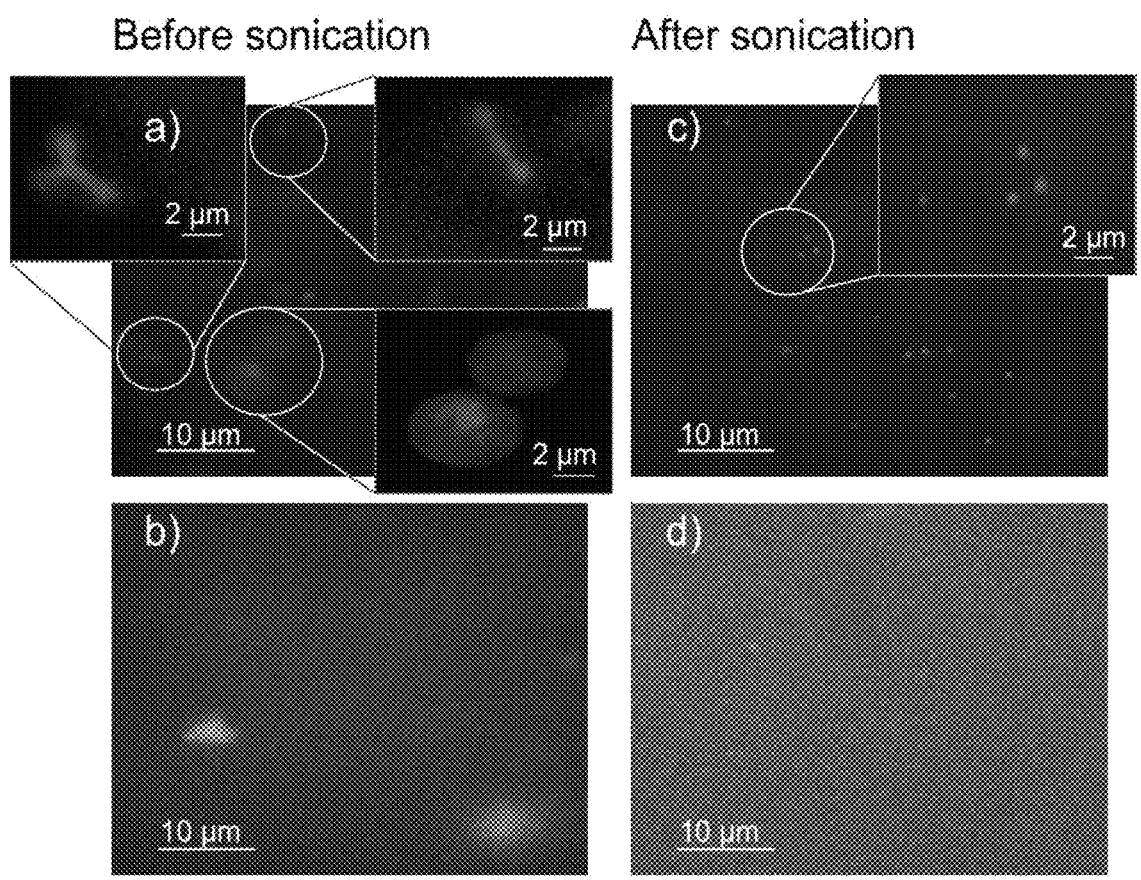

FIG. 7. Analysis of the RBC/aspirin complexes. a) Shows all reflectivity curves for complexes containing between 0 and 3 mM ASA. b) The pattern for the 2.5 mM sample is well fit by three series of peaks corresponding to $l_o$, ld and peptide domains. c) The location of the ASA molecule is determined by comparing the electron density of a pure RBC membrane with a low concentration of 1 mM ASA. Aspirin is found to partition the $l_o$ lipid domains of RBC membranes and locate in the head group region, at |z|-values of 22.8 Å. d) Small partitioning of aspirin is observed in ld lipid domains, indicative that aspirin preferably interacts with $l_o$ domains. e) Lamellar spacing, $d_z$, and membrane thickness, dHH of the $l_o$ lipid domains decrease significantly with increasing ASA concentration until thickness of $l_o$ and ld domains coincide.

Figure 8:
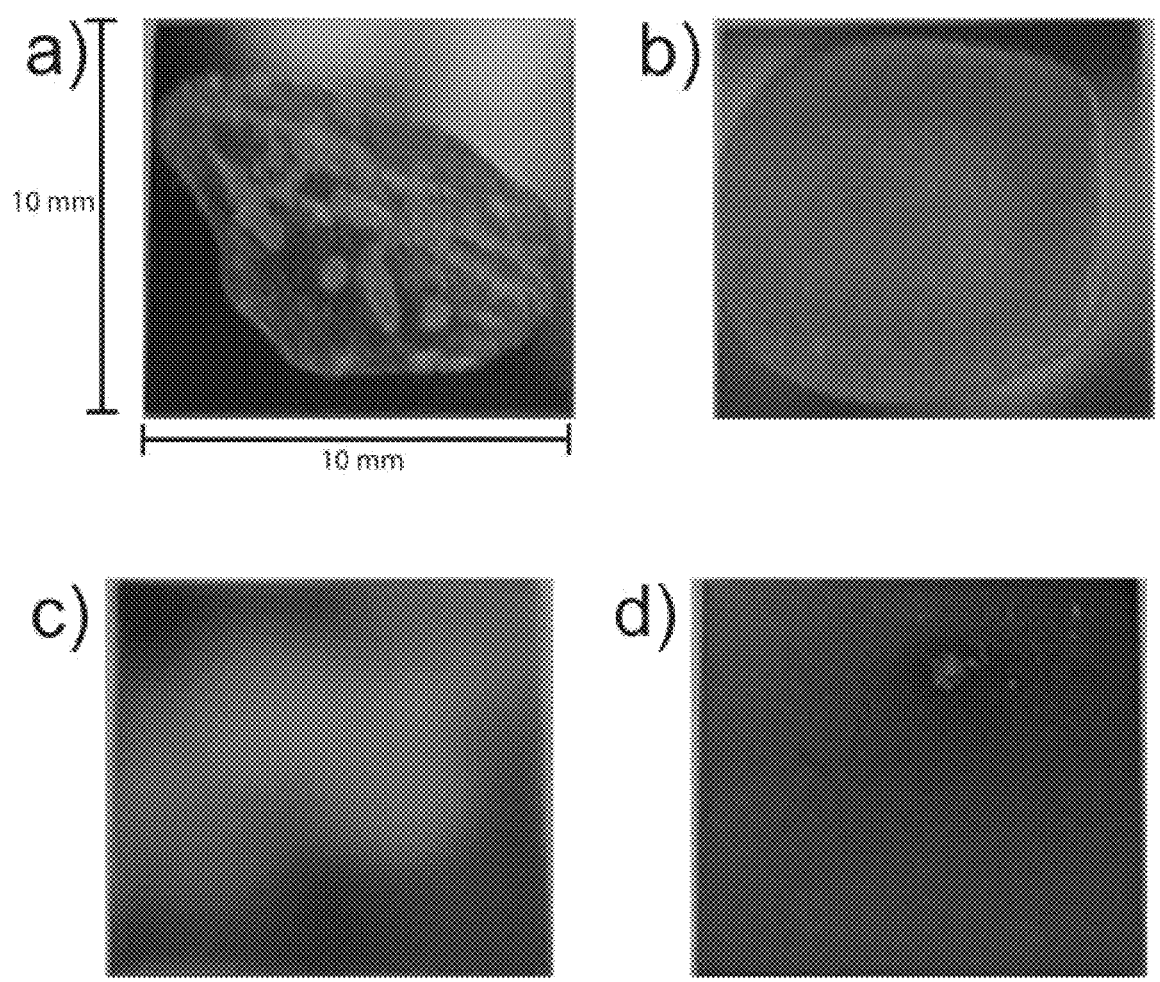

FIG. 8. The structural findings are summarized in cartoons of pure RBC membranes (a) and RBC membranes containing aspirin (b). While domains of saturated, unsaturated lipids and coiled-coil peptides are observed in pure RBC membranes, with significantly different membrane thicknesses, the addition of aspirin leads to an overall thinning of the membranes and an increase of the lipid spacings, indicative of a fluidification. Aspirin mainly interacts with the $l_o$ lipid domains. Structural parameters determined in this study are given in the figures.

Figure 9:
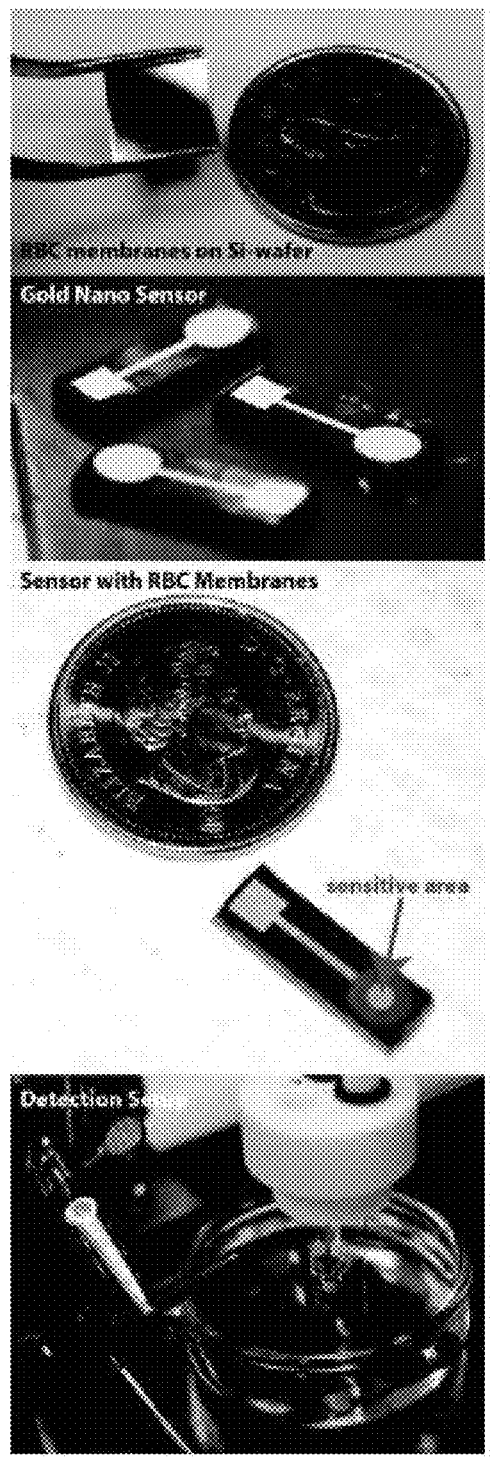

FIG. 9. Nanostructured gold electrodes with RBC membranes applied to the sensors.

Figure 10:
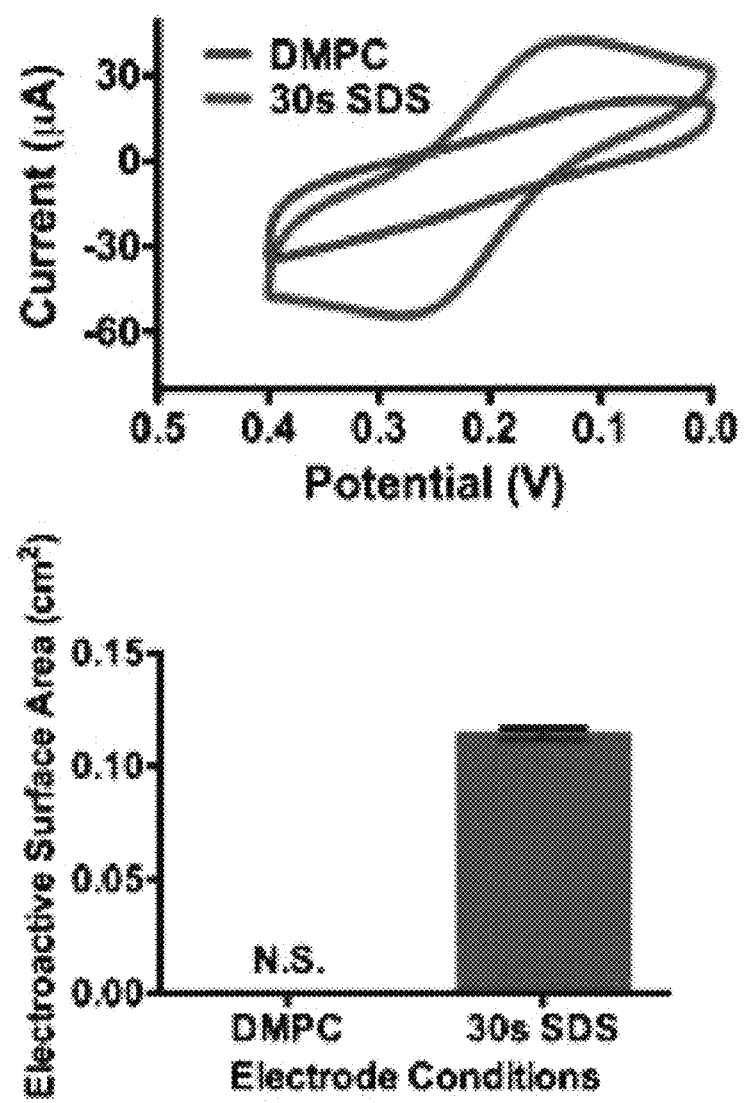

FIG. 10. Modelling hemolytic activity based on membranes disrupted using the surfactant, sodium dodecyl sulfate (SDS).

Figure 11:
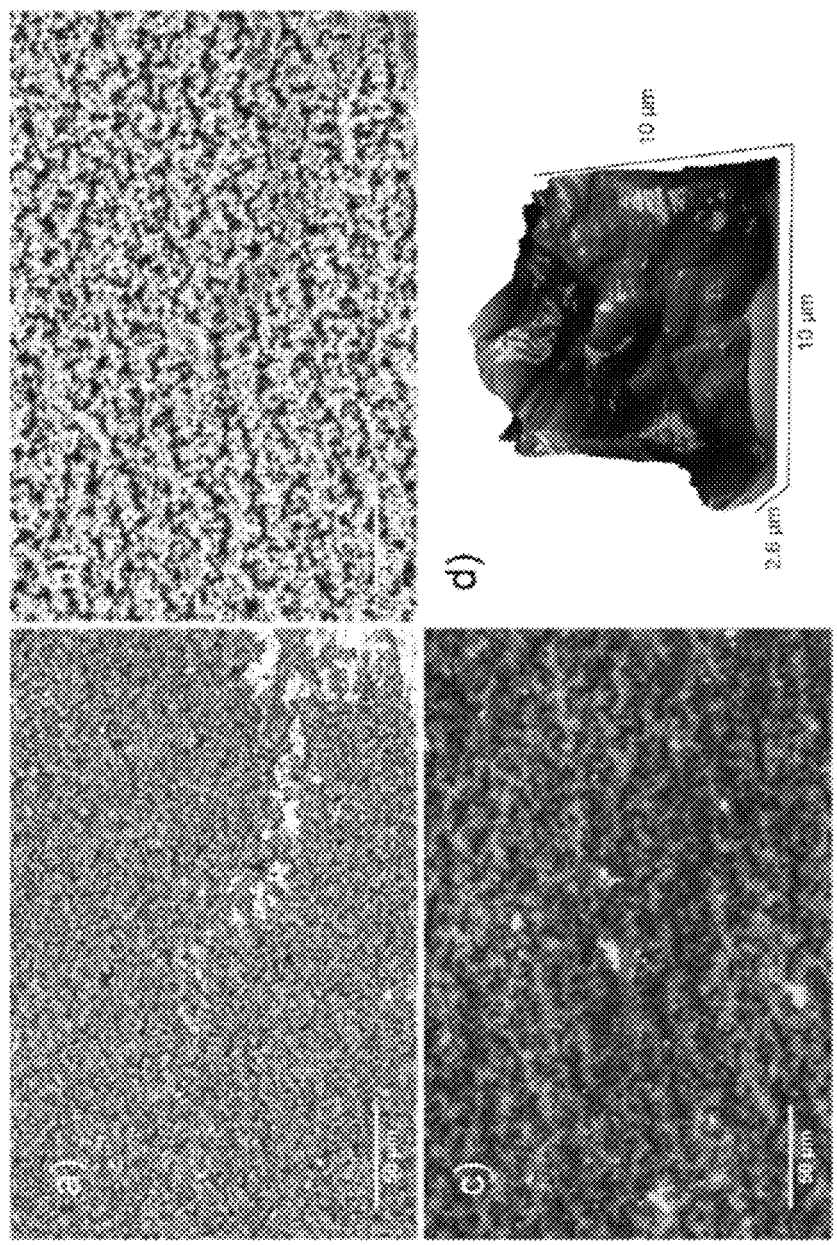

FIG. 11. Microscopy images of an exemplary biosensor. (a) and (b) are standard images at different resolutions. (c) shows a fluorescent image where the red blood cell membranes are illuminated, indicating that the red blood cell membranes are annealed to the sensor. (d) shows an electron microscopy image of an enlarged section of the surface of multi-lamellar structure on a biosensor.

Figure 12:
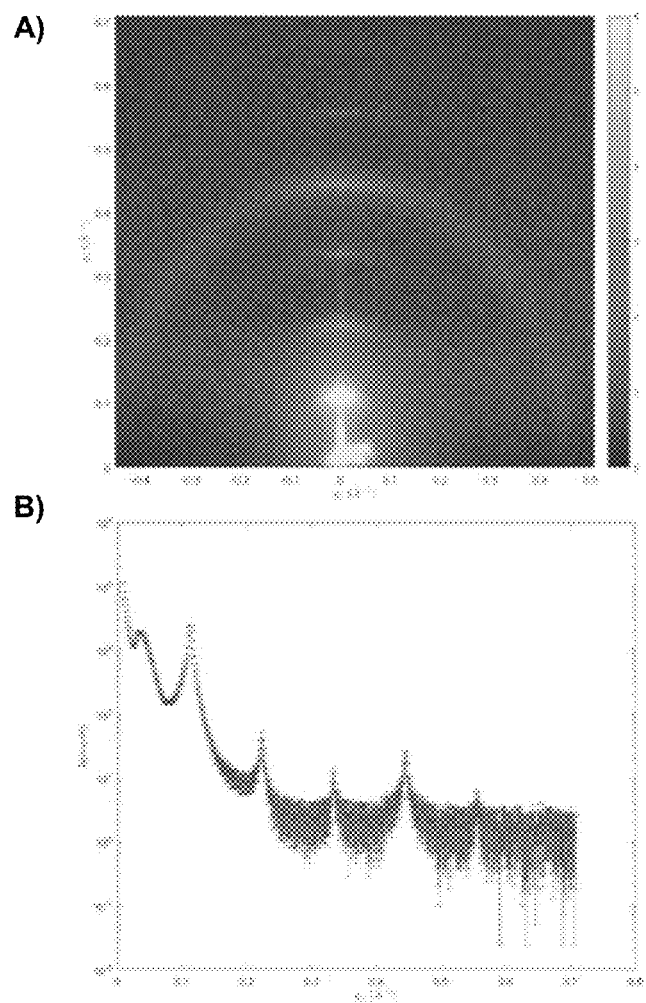

FIG. 12 shows the improved quality of the membrane coating obtained using the protocol of Example 3. (a) shows a 2D x-ray image, (b) shows the reflectivity Bragg peaks.

DETAILED DESCRIPTION

Unless otherwise indicated, the definitions and embodiments described in this and other sections are intended to be applicable to all embodiments and aspects of the present application herein described for which they are suitable as would be understood by a person skilled in the art.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "and/or" as used herein means that the listed items are present, or used, individually or in combination. In effect, this term means that "at least one of" or "one or more" of the listed items is used or present.

In one aspect, there is provided a biosensor comprising a multi-lamellar lipid membrane structure. An exemplary multi-lamellar lipid membrane structure comprising two lipid bilayers is shown in FIG. 5. In one embodiment, the biosensor comprises a solid substrate having a lipid bilayer compatible surface and a multi-lamellar lipid membrane structure derived from a plurality of biological cells and localized on the lipid bilayer compatible surface. In one embodiment, there is an aqueous layer interposed between each lipid layer of the multi-lamellar lipid membrane structure.

In one embodiment, the substrate comprises a lipid bilayer compatible surface that is selected or configured to allow for the localization of the multi-lamellar lipid membrane structure adjacent to the surface. In a preferred embodiment, the surface is a planar surface. In one embodiment, the lipid bilayer compatible surface is hydrophilic.

In one embodiment, the multi-lamellar lipid membrane structure may be derived or prepared from red blood cells. In one embodiment, the multi-lamellar lipid membrane structure is derived from red blood cell ghosts. As shown in FIG. 1 and detailed in the Examples, incubating a preparation of red blood cell ghosts on a lipid bilayer compatible surface results in the annealing of the individual cell ghosts into a multi-lamellar lipid membrane structure adjacent to the lipid bilayer compatible surface. In one embodiment, the multi-lamellar lipid membrane structure is a bilayer. In one embodiment, the multi-lamellar lipid membrane structure is made of two stacked lipid bilayers.

In one embodiment, the multi-lamellar lipid membrane structure is formed by incubating the lipid bilayer compatible surface with the preparation of red blood cell ghosts, wherein the red blood cell ghosts anneal to form the multi-lamellar lipid membrane structure. In one embodiment, the cell ghosts are incubated at a temperature greater than about 30° C., 35° C., or 40° C. In one embodiment, the cell ghosts are incubated at a temperature between about 30° C. and 60° C. In one embodiment, the temperature is about 30° C., 35° C., 37° C., 40° C., 45° C. or 50° C. In one embodiment the temperature is between about 35° C. and 55° C., or between about 35° C. and 40° C.

As demonstrated in the Examples, the formation of a multi-lamellar lipid membrane structure is improved under humid conditions. Accordingly, in one embodiment the cell ghosts are incubated at a relative humidity greater than 50%. In one embodiment, the relative humidity is greater than 50%, 60%, 70%, 80%, 85% or 90%. In one embodiment, the relative humidity is between about 70% and 100%, optionally between about 80% and 95%.

In one embodiment, the biological cells, optionally cell ghosts, are incubated in the presence of a salt or salt solution. For example, in one embodiment the substrate is incubated on a platform above a salt solution. In one embodiment, the salt solution is a potassium sulfate solution, optionally a saturated potassium sulfate solution. In one embodiment, the salt is potassium sulfate, lithium chloride, potassium acetate, magnesium chloride, potassium carbonate, magnesium nitrate, sodium chloride, potassium chloride, potassium nitrate, potassium sulfate, or combinations thereof.

Various materials known in the art may be used as the solid substrate for the biosensor. For example, the solid substrate may be made of a material such as silicon dioxide ($SiO_2$), glass, polydimethylsiloxane (PDMS), polymethyl methacrylate (PMMA), and/or polycarbonate (PC). In one embodiment, the solid substrate comprises $SiO_2$.

In one embodiment, the solid substrate comprises a lipid bilayer compatible surface. Optionally, the lipid bilayer compatible surface may be made of the same material as the solid substrate or a different material. In one embodiment, the lipid bilayer compatible surface is hydrophilic. In one embodiment, a hydrophilic surface promotes the formation of the multi-lamellar lipid membrane structure adjacent to the surface on the biosensor.

Various methods known in the art may be used to render a surface of the solid substrate hydrophilic. For example, the lipid bilayer compatible surface may comprise acid treated $SiO_2$ or poly-lysine. In one embodiment, the surface may be plasma-treated to render the surface hydrophilic by oxidation and formation of hydroxyl (OH) groups.

Acid-treatment may be performed by various methods known in the art. For example, in one embodiment $SiO_2$ is cleaned by immersion in a sulfuric acid ($H_2O_2$) mixture (volume fraction of 70% concentrated $H_2SO_4$, 30% $H_2O_2$ at 40° C.) for 30 min).

In one embodiment, the biosensor comprises at least one electrode. In one embodiment, the electrode comprises all or part of the lipid bilayer compatible surface. The electrode may comprises gold, carbon, gold, silver, copper, aluminum, graphite, brass, platinum, palladium, titanium or a combination thereof. In one embodiment, the electrode comprises gold. For example, as demonstrated in Example 2 a biosensor may be formed by using a solid substrate comprising an electrode of functionalized gold that serves as the lipid bilayer compatible service. In another embodiment, the biosensor may comprise an electrode comprising a functionalized metal such as gold, copper, silver, or platinum.

Optionally, in one embodiment the biosensors described herein include at least one reference electrode.

It will be appreciated by a person skilled in the art that various means for applying potential and measuring current can be used in combination with the biosensors described herein that comprise one or more electrodes. In an embodiment, the biosensor is operatively connected to a power supply or voltage source, and/or a detector for detecting a change in current and/or potential, optionally in response to a sample.

In one embodiment, the biosensor comprises a microfluidic device, well, or channel for receiving a sample. In one embodiment, the microfluidic device, well, or channel is in fluid communication with the lipid bilayer compatible surface. For example, in one embodiment, the microfluidic device, well or channel is in fluid communication with at least a portion of the surface of an electrode as described herein.

In another aspect, the there is provided an array comprising a plurality of the biosensors described herein.

In another aspect, there is provided a method of detecting membrane disruption activity in a sample. In one embodiment, the method comprises:
 contacting a biosensor as described herein with the sample; and
 detecting a change in the multi-lamellar lipid membrane structure in response to the sample.

Various methods known in the art may be used to detect a change in the multi-lamellar lipid membrane structure. For example, in one embodiment the change in the multi-lamellar lipid membrane structure is detected optically. In another embodiment, the change in the multi-lamellar lipid membrane structure is detected using x-ray scattering techniques such as x-ray diffraction.

In one embodiment, the change is detected using voltammetry, optionally cyclic voltammetry, chronoamperometry, differential multi pulse voltammetry, double potential pulse techniques or additive differential pulse voltammetry.

In one embodiment, the sample further comprise a redox-indicator. The redox-indicator may be, for example, ferricyanide, o-dianisidine, viologen, 2,2'-biyridine, viologen, thionine, safranin, indigo carmine, or N-Phenylanthranilic acid. In an embodiment, the redox indicator is ferricyanide.

The sample may be any sample for which information regarding the presence or absence of membrane disruption activity in the sample is desired. For example, in one embodiment the sample is an environmental sample such as a water sample or food sample. In one embodiment, the sample comprises a test compound or agent and the method is for screening the test compound or agent for membrane disruption activity, optionally for hemolytic activity. In one embodiment, the sample is a biological sample, such as biological sample from a subject. In an embodiment, the biological sample may include is blood, tissue samples, tissue biopsies, samples taken from tissue culture, biological fluids, tissue extracts, freshly harvested cells, lysates of cells which have been incubated in cell cultures. In one embodiment, the biological fluid is urine, blood, a component of blood such as plasma or serum, sputum, or cerebral spinal fluid.

In an embodiment, the membrane disrupting activity is hemolysis, membrane fluidity, membrane elasticity, or membrane permeability.

In an embodiment, the change detected in the multi-lamellar lipid membrane structure is compared to a control. In one embodiment, a difference or similarity between the change detected in the multi-lamellar lipid membrane structure in response to the sample and the control may be indicative of the presence or absence of membrane disrupting activity in the sample such as a hemolytic agent. In one embodiment, the control is representative of a change in the multi-lamellar lipid membrane structure in response to a hemolytic agent, and a similarity between the change detected in response to the sample and the control is indicative of the presence of a hemolytic agent in the sample.

In another aspect, the multi-lamellar lipid membrane structures described herein are useful for the investigation of molecules or compounds in association with a lipid membrane. For example, in one embodiment, there is provided a method comprising contacting a multi-lamellar lipid membrane structure as described herein with a molecule or compound, bombarding the multi-lamellar lipid membrane structure and measuring the resultant diffraction pattern.

EXAMPLES

The following non-limiting examples are illustrative of the present application:

Example 1: Preparation and Fabrication of Multi-Lamellar RBC Membranes on Solid Support Materials and Methods Optical Microscopy and Total Internal Reflection Fluorescence Microscopy (TIRF)

The images were acquired through a LEICA DMI6000 B inverted microscope equipped with a Spectral Laser Merge Module for multi-wavelength illumination (Spectral, Richmond Hill, ON), adaptive focus control, a motorized X-Y stage (MCL Micro-Drive, Mad City Labs Inc., Madison, Wis.), a piezo X-Y-Z stage (MCL Nano-Drive, Mad City Labs Inc., Madison, Wis.), a LEICA 100×/1.47NA oil-immersed TIRF objective and an Andor iXon Ultra EMCCD camera. Excitation was provided by 488 and 647 nm diode-pumped solid-state lasers with 40 mW and 60 mW output power respectively (Spectral, Richmond Hill, ON). Alexa Fluor 488 labelled phalloidin (Invitrogen) was used to label the F-actin network and 1,1'-Dioctadecyl-3,3,3',3'-Tetramethylindocarbocyanine Perchlorate (Sigma-Aldrich) was used to label the membranes.

UV-Vis Spectroscopy

Ultraviolet-visible spectroscopy (UV-vis) was obtained using a M1000Pro Plate reader from Tecan. The technique is depicted in FIG. 2c): the absorption of light in the visible and adjacent (near-UV and near-infrared) ranges is detected. Hemoglobin shows characteristic absorption lines at 335±0.4 nm, 416.4±0.2 nm 543±0.8 nm and 577±0.4 nm [77]. In order to prepare a sufficiently diluted RBC solution, 50 µL of the erythrocytes fraction was mixed with 1 mL PBS. 400 µL of this solution was afterwards diluted with 400 µL PBS. This dilution procedure has been repeated three times. For the measurement, a 96-plate from Costar was used. 200 µL of the diluted blood solution, the ghosts solution and the RBC solution were filled in the chambers of the plate. The absorption spectrum for each sample was scanned for wavelengths between 310 nm and 800 nm.

X-Ray Diffraction

X-ray scattering data was obtained using the Biological Large Angle Diffraction Experiment (BLADE) in the Laboratory for Membrane and Protein Dynamics at McMaster University. BLADE uses a 9 kW (45 kV, 200 mA) CuKα rotating anode at a wavelength of 1.5418 Å. Both source and detector are mounted on movable arms such that the membranes stay horizontal during the measurements. Focusing multi-layer optics provides a high intensity parallel beam with monochromatic X-ray intensities up to $10^{10}$ counts/(mm²·s). This beam geometry provides optimal illumination of the solid supported membrane samples to maximize the scattering signal. A sketch of the scattering geometry is shown in FIG. 5a). Note that there is no risk of sample damage using this in-house technique because of the large beam size and relatively low intensity of the X-ray beam as compared to synchrotron sources.

The result of an X-ray experiment is a 2-dimensional intensity map of a large area of the reciprocal space, as sketched in FIG. 5. The corresponding real-space length scales are determined by $d=2\pi/Q$ and cover length scales from about 2.5 to 100 Å. All scans were measured at 28° C. and 50% relative humidity (RH) hydration. As depicted in FIG. 5a), the wafers were oriented in the X-ray diffractometer, such that the $q_\parallel$-axis probed lateral structure, parallel to the wafer surface, and the perpendicular axis, $q_z$, probed out-of-plane structure, perpendicular to the substrate.

The experimental errors were determined as follows: Errors for peak positions, peak width and peak height are determined as the fit standard errors, corresponding to 95% confidence bounds, equivalent to 2 standard deviations, σ. Errors for calculated parameters, such as peak area, were then calculated by applying the proper error propagation.

Calculation of Electron Densities

The out-of-plane structure of the membrane was determined using specular reflectivity. The relative electron density, ρ(z), is approximated by a 1-dimensional Fourier analysis [51, 78].

$$\rho(z) = \frac{2}{d_z}\sum_{n=1}^{N}\sqrt{I_n q_n}\, v_n \cos\left(\frac{2\pi n z}{d_z}\right).$$

N is the highest order of the Bragg peaks observed in the experiment. The integrated peak intensities, I, are multiplied by q, to receive the form factors, F(q,) [51, 78]. The bilayer form factor $F(q_z)$, which is in general a complex quantity, is real-valued in the case of centro-symmetry. The phase problem of crystallography, therefore, simplifies to the sign problem $F(q_z)=\pm|F(q_z)|$ and the phases, v, can only take the values ±1. The phases, v, are needed to reconstruct the electron density profile from the scattering data following Eq. (1). When the membrane form factor $F(q_z)$ is measured at several $q_z$ values, a continuous function, $T(q_z)$, which is proportional to $F(q_z)$, can be fitted to the data [51, 78].

$$T(q_z) = \sum_n \sqrt{I_n q_n}\, \text{sinc}\left(\frac{1}{2}d_z q_z - \pi n\right).$$

Once an analytical expression for $T(q_z)$ has been determined from fitting the experimental peak intensities, the phases v, can be assessed from $T(q_z)$. The phase array v, =[−1−1 1−1 1] was used for all samples.

The electron densities determined by Eq. (1) are on a relative scale. In order to compare the electron densities in FIGS. 6c) and 7c), ρ in the membrane centre at z=0 was set to 0 and the electron density at the boundaries (z values between 25 and 30 Å depending on the lamellar spacing), which probe the water layer between the stacked membranes, were scaled to the electron density of water of ρ=0.33 e⁻/Å³.

Membrane Orientation

To determine the degree of orientation of the membranes in the stack the correlation peak intensities were integrated as function of the meridonal angle φ (the angle relative to the $q_z$ axis). The corresponding intensity was fit with a Gaussian distribution centered at 0, which was then used to calculate the degree of orientation using Hermans orientation function:

$$H = \frac{3<\cos^2\delta>-1}{2}.$$

The degree of orientation, H, of the RBC membranes was measured to be 90.9%.

Determination of Domain Sizes

The average size of the different lipid and peptide domains was estimated from the widths of the corresponding in-plane correlation peaks in FIG. 5d) by applying Scherrer's equation [79]:

$$L = \frac{0.94\lambda}{B(2\theta)\cos(\theta)},$$

where $\lambda$ is the wavelength of the X-ray beam, $\theta$ is the diffraction angle and $B(2\theta)$ is the width of the correlation peak in radians. Scherrer's equation is an established way to estimate crystallite sizes of up to ẏ100 nm in X-ray diffraction experiments. Note that the equation has limitations to quantitatively determine sizes of small domains of a few nanometers, only. The determined values present upper limits of the domain sizes.

The preparation protocol is schematically depicted in FIG. 1 and consists of two main parts: In the first step, RBC ghosts are produced from blood samples. In the second step, these RBC ghosts are applied onto silicon wafers and annealed to form multi-lamellar RBC membrane stacks.

Preparation of Ghosts

The preparation of RBC ghosts was first published in 1963 by Dodge, Mitchell and Hanahan [1]: 10 mL of venous blood were drawn from a participating individual. The blood was collected in venous blood collection tubes from BD (Product Number: BD 367874), coated with sodium heparin as anticoagulant. The tube was centrifuged at 3,000 g for 10 min at room temperature. After this process, a clear separation between an erythrocyte fraction and a plasma fraction was observed. The white blood cells and platelets form a layer between those two fractions.

In the original protocol, the RBC solution was then filtered by a procedure by Beutler, West and Blume [43], where the RBC solution is pushed through a cellulose filter. This process was suggested to produce pure erythrocyte preparations without the remaining leucocytes and platelets. While this protocol is well established and widely used in blood cell investigations (see, for instance, [44] for a recent review), the ghost solution produced by this protocol did not result in well-developed multi-lamellar lipid membrane stacks when applied on silicon wafers. Cellulose particles were observed under the microscope in the solution after passing through the filter, which likely inhibit the formation of well-ordered membrane stacks.

In order to avoid contamination with cellulose, the RBC solution was purified through centrifugation using the following protocol: The supernatant in the separated blood sample was removed using a pipette. PBS was added to the precipitate to achieve a volume of 10 mL and centrifuged at 3,000 g for 10 min. This process was repeated twice.

50 μL of the RBC solution was then mixed with 1 mL of buffer solution in a 1.5 mL reaction tube. For the buffer, 16 mL of PBS and 484 mL of 18.2 M Ω·cm ultra-pure water were mixed and stored at 0° C. The solution was buffered with potassium hydroxide and hydrochloric acid to a pH of 8. This creates a hypotonic solution for the RBCs, resulting in an influx of water into the cells and their lysis. The diluted solution is vortexed for 10 s to prevent clumping. After vortexing, the reaction tube is immediately placed in ice for 30 min to slow down the re-closing of the burst cells.

Samples were then centrifuged at 18,000 g for 30 min at 0° C. After the centrifugation, a pellet is formed at the bottom of the reaction tube. The supernatant was removed by pouring the reaction tube in a beaker. 1 mL buffer solution was added to the pellet and the solution was vortexed for 10 s and centrifuged for 15 min at 18,000 g and 0° C. This process of centrifugation and removal of the supernatant was repeated 4 times. During this washing, most of the hemoglobin is removed, resulting in a transparent, colorless solution. FIG. 2a) shows images of the reaction tube after different numbers of washing steps.

The removal of hemoglobin was quantitatively checked using ultraviolet-visible spectroscopy (UV-vis). The corresponding data is shown in FIG. 2 b). The characteristic hemoglobin absorption bands at 335 nm, 416.4 nm 543 nm and 577 nm decrease in every step; the hemoglobin content of the final solution was found to contain less than 2% of the original content.

This procedure results in solutions with typical mass concentration of RBC's of ~0.3 mg/mL. To increase the concentration, pellets from 24 such reaction tubes were collected and centrifuged at 18,000 g for 15 min. The supernatant was removed and the tube was refilled with buffer solution to the 1 mL mark of the tube. This results in a solution with a final mass concentration of ~7 mg/mL. The ghost solution was analyzed by fluorescence microscopy, as shown in FIG. 3 a) and b). The red blood cell membrane was fluorescently labeled in part a) using 1,1'-Dioctadecyl-3,3,3',3'-Tetramethylindocarbocyanine Perchlorate (DiI). The image shows a mix of multi-lamellar and uni-lamellar ghosts with a highly irregular shape and a large distribution of shapes and sizes, from round to long, more chain-like objects including vesicles that contain several smaller vesicles. These shapes are likely related to the presence of a cytoskeleton, whose main components are spectrin and actin in RBC [45]. To analyze this network, Alexa Fluor 488 labelled phalloidin was used to label the F-actin network in FIG. 3 b). Structures of ~5 μm were observed, indicative of the presence of actin.

As indicated below, the variation in size and shape of the ghosts, and the presence of an actin network likely prevents the formation of well defined, solid supported multi-lamellar RBC. To achieve a more uniform distribution of vesicle sizes and shapes, the RBC solution was tip sonicated 10 times for 5 s, each, in order to form small uni-lamellar vesicles (SUVs). The result of the sonication process is shown in FIG. 3c) and d). In part c), the membrane was fluorescently labeled using DiI. Small dots were observed, indicative of small uni-lamellar vesicles of ~50 nm, beyond the resolution limit of the microscope.

The actin concentration was analyzed by labelling with Alexa Fluor 488 labelled phalloidin. After sonication, no more particles were observed within the resolution of the microscope used. In order to separate the SUVs and remaining actin, the solution was centrifuged for 30 min at 20,000 g. Since SUVs can only sediment in ultra-centrifuges at 120,000 g when centrifuged for more than 30 min [46], the pellet contains actin polymers and potential larger and multi-lamellar vesicles, while the SUVs stay in the supernatant. This supernatant was found to be ideal for the formation of solid supported, multi-lamellar RBC membranes, as will be discussed below.

Silicon Wafer Preparation

All membranes were prepared on single-side polished silicon wafers. 100 mm diameter, 300 μm thick silicon wafers were pre-cut into 10×10 mm² chips. The wafers were functionalized for deposition of the ghost solution by either preparing a hydrophobic or hydrophilic surface. To create a hydrophobic silicon surface, the wafers were pre-treated by sonication in dichloromethane (DCM) at 40° C. for 25 min.

This treatment removes all organic contamination and leaves the surface in a hydrophobic state. Each wafer was then thoroughly rinsed three times by alternating with ~50 mL of ultra-pure water with a resistivity of 18.2 MΩ·cm and HPLC grade methanol.

To create a hydrophilic state, the wafers were cleaned by immersion in an $H_2O_2$ sulfuric acid mixture (volume fraction of 70% concentrated $H_2SO_4$, 30% H2O2 at 40° C., Piranha™ solution) for 30 min on a 3D orbital shaker (VWR) set to tilt angle 1 and speed 15). This strongly oxidizing combination removes all organic contaminants on the surface, but does not disturb the native silicon oxide layer. Each wafer was then thoroughly rinsed with ~50 mL of ultra-pure water with a resistivity of 18.2 MΩ·cm.

Fabrication of Highly Oriented, Multi-Lamellar Solid Supported RBC Membranes.

The ghost solution did not spread well on hydrophobic silicon wafers, as shown in FIG. 4a). For this wafer, 100 µL of concentrated ghosts solution was applied onto a 10×10 mm² hydrophobic silicon wafer mounted on a leveled hot plate at a temperature of 40° C. The solution was applied slowly using a 100 µL syringe to avoid spill, and the wafer typically dried within ~10 min. The membrane film was found not to cover the entire wafer and showed several wrinkles.

Slowly drying the solution to allow more time for the solution to spread and membranes to form was achieved by placing the wafers in a leveled desiccator for 5 days at 97.6±0.5% relative humidity using a saturated K2 SO4 salt solution. The slow drying resulted in a smoother film, however, still incomplete coverage of the substrate, as shown in FIG. 4b). FIG. 4c) shows a hydrophilic wafer prepared by applying 100 µL of concentrated SUV solution and dried for 5 days at 97.6±0.5% relative humidity. The solution covered the entire wafer indicating a homogeneous mass distribution. Only weak signals of membrane stacking in this sample were detected and thus the inventors picture the morphology of the membranes as depicted in FIG. 1d), as uni-lamellar vesicles that have been dried out on the silicon substrate. This situation is similar to the preparation of single solid supported bilayers through vesicle fusion [47, 48], where small bilayer patches initially develop on the substrate, and eventually undergo a transition into a large uniform single bilayer [47]. Substrates are typically annealed for 72 h at 55° C. in an oven in air. The energy barrier for forming a lamellar structure can be overcome through gentle heating and the lamellar membrane organization becomes energetically more favorable, as it minimize the bending energy.

However, using the same procedure and heating the RBC membranes in an oven led to destruction of the membrane film. The silicon chips were, therefore, incubated at different temperatures and under relative humidities between 50% and 100% RH by placing them in a closed container and exposure to different saturated salt solutions. The best results were obtained when the RBC chip was annealed at 50° C. and 95.8±0.5% relative humidity in a saturated $_{K2SO4}$ salt solution for 5 days, which resulted in the photo in FIG. 4 d). In this protocol, annealing of the RBC membranes at high temperature and humidity leads to the formation of lamellar membrane structures through membrane fusion.

Preparation of RBC/Aspirin Complexes.

In order to prepare complexes of RBC membranes containing increasing amounts of aspirin, a solution of 9 mg/mL acetylsalicylic acid (molecular weight 180 g/mol) in 18.2 MΩ·cm water was prepared. 2 µL, 3 µL, 4 µL, 5 µL, and 6 µL of this solution were added to 100 µL of the final ghosts solution resulting in acetylsalicylic acid concentrations of 1 mM, 1.5 mM, 2 mM, 2.5 mM and 3 mM. The resulting solutions were applied onto silicon wafers and dried slowly and incubated for 5 days following the above protocol.

The molar concentration of ASA in the RBC mem-branes can be estimated as follows: between 2 and 5 µL of the 9 mg/mL ASA solution were added to the membrane solution, resulting in between $1 \cdot 10^{-7}$ and $2.5 \cdot 10^{-7}$ mol. 100 µL of the 7 mg/mL RBC contain $\sim 2 \cdot 10^{-6}$ mol (when assuming an average molecular weight of the membranes. of 400 g/mol). This results in molar ASA concentrations between 5-10 mol %, i.e., 1 ASA molecule per 10 to 20 lipid molecules. This ASA concentration is elevated as compared to plasma concentrations of typically less than 1 mol %, however, comparable to ASA concentrations typically used in the literature [49].

Results and Discussion

Molecular Structure and Properties of RBC Membranes.

In this section, X-ray diffraction was used to determine the morphology and molecular structure of the RBC membranes. The main findings can be summarized as follows.

The protocol presented in this paper produces highly oriented, multi-lamellar RBC membranes on silicon wafers, which are highly suited for study using biophysical techniques in order to provide detailed molecular level information.

RBC membranes consist of nanometer-sized liquid ordered ($l_o$) and liquid disordered (ld) lipid domains and α-helical coiled-coil peptide domains, at ratios of 30.4% $l_o$, 45.0% ld and 24.8% coiled peptides.

As the membranes are oriented with their membrane plane parallel to the silicon substrate, the in-plane and out-of-plane structure could be determined separately but simultaneously. A schematic of the X-ray diffraction setup is shown in FIG. 5a). FIG. 5b) shows the 2-dimensional X-ray diffraction pattern of a sample pre-pared with the final preparation protocol. The organization of the membranes normal to the silicon wafer is observed along the $q_z$-axis, while molecular organization in the plane of the membranes parallel to the substrate is observed along the q∥-direction. Cuts of the diffracted intensity along the out-of-plane and in-plane direction are shown in FIG. 5c) and d).

Structure Perpendicular to the Membrane Plane

A lamellar membrane structure, i.e., a stack of membranes, where the bilayers are organized parallel to each other, results in a series of equally spaced and well defined Bragg reflections in diffraction experiments [8], corresponding to the 'fundamental' and the 'overtones'. The well-developed Bragg peaks along the out-of-plane axis in FIG. 5 c) are indicative of a lamellar organization of the RBC membranes on the substrate. The fundamental reflection for each series is colored in the Figure. Following Bragg's law ($q_z=2\pi/d_z \cdot n$), the lamellar spacing, $d_z$, can be determined from the slope of the curve when plotting $q_z$ vs. the order of the Bragg peak, n. This is shown in FIG. 6a) and 3 $d_z$-spacings were determined: $d_{lo}$=59.2 Å, $d_{ld}$=51.6 Å and $d_p$=40.6 Å.

Electron density profiles, ρ(z), of the bilayers were determined through Fourier analysis of the out-of-plane Bragg peaks, as described in the Materials and Methods section, and are shown in FIG. 6b). The electron rich head group can be identified by the absolute maximum in the electron density profile at z~22 Å. σ monotonically decreases to the bilayer center at z=0, where CH3 groups typically reside in the center, with a low electron density. The electron density of the $_{dlo}$=59.2 Å domain (blue curve) corresponds well to a lipid bilayer with lipids in the gel state with lipid chains in an all-trans configuration [50, 51], and was, therefore, assigned to lipids in lo domains. These domains are enriched in cholesterol making them more ordered and thicker [32, 35].

The electron density corresponding to the $d_{ld}$=51.6 Å spacing (green curve) agrees well with the electron density reported for fluid lipid bilayers, where the structure of the lipid tails in the hydrophobic membrane core is dominated by gauche-defects, as reported for instance by [52, 53]. These signals were assigned to domains of $l_d$ lipids.

The 3rd spacing of $d_p$=40.6 Å is significantly smaller and the electron density shows an almost constant density in the hydrophobic membrane core. This density profile is well described by α-helical peptide coiled-coils, which are embedded in the membranes [26].

Lamellar spacings, $d_z$, membrane thicknesses, $d_{HH}$, and the thicknesses of the water layer, $d_w$, were determined from the electron densities and are listed in Table 1.

In-Plane Membrane Structure

Three peaks at $q\|$=0.58 Å$^{-1}$, $q\|$=1.35 Å$^{-1}$ and $q\|$=1.55 Å$^{-1}$ were observed in the in-plane diffraction in FIG. 5d). These peaks fit well to distances between peptides and lipids, observed in previous investigations in single and multicomponent artificial and biological membranes [26, 35, 52, 54-56]. The peaks at $q\|$=1.35 Å$^{-1}$ and $q\|$=1.55 Å$^{-1}$ are in good agreement with structural features reported in model lipid membranes in their well-ordered gel and fluid phases, where the lipids tails take an all-trans conformation (gel) or are dominated by gauche defects (fluid). A correlation peak at ~1.5 Å$^{-1}$ was reported in the gel phase of saturated phospholipid membranes, such as DMPC (Dimyristoyl-sn-glycero-3-phosphocholine) and DPPC (Dipalmitoyl-sn-glycero-3-phosphocholine) [32, 50, 54, 57]. Unsaturated lipids were reported to order in a structure with slightly larger nearest neighbor tail distances, leading to an acyl-chain correlation peak at ~1.3 Å$^{-1}$, as reported for DOPC and POPC [27, 58]. These correlation peaks were assigned to the $l_o$ and $l_d$ lipid components of the plasma membranes.

The in-plane peaks are the result of a hexagonal packing of the lipid tails in the hydrophobic membrane core (planar group p6) [32]. The distance between two acyl tails is determined to be $a=4\pi/(\sqrt{3}q)$, where $q_\|$ is the position of the corresponding correlation peak. The area per lipid chain is obtained to $AT=(\sqrt{3}/2)\ a^2$ Lipid tail distances in $l_o$ and $l_d$ domains and lipid tail areas are listed in Table 1. Distances and areas in the lo domains are smaller, as lipid tails in their all-trans configuration are straighter and pack tighter than $l_d$ tails, dominated by gauche defects.

Membrane peptides are often organized in bundles, whose structure is dominated by α-helical coiled-coils [26, 59-62]. Coiled coils consist of α-helices wound together to form a ropelike structure stabilized by hydrophobic interactions, found in about 10% of the proteins in the human genome [63]. The main feature of this motif is a ~10.8 Å ($q\|$~0.58 Å$^{-1}$) equatorial reflection corresponding to the spacing between adjacent coiled-coils [64-66]. The volume fractions of the peptide, the $l_o$ and $l_d$ lipid domains were determined from the integrated peak intensities of the lipid and peptide signals in FIG. 5d) to 30:45:25 ($l_o$ lipids:$l_d$ lipids:coiled peptides).

While RBC membranes were reported to consist of ~52% proteins and ~40% lipids [4], the values above indicate a higher fraction of lipids (and cholesterol). The technique is not sensitive to monomeric short peptides, but to the packing of peptide helices, only. These helical regions are likely part of larger trans-membrane proteins. The molecular structure of the RBC membranes is pictured in FIG. 8a).

In early X-ray diffraction studies of human erythrocytes membranes [67, 68] ghosts were prepared using the Dodge protocol and pellets of the final preparation were imaged. Diffraction patterns with lamellar periodicities between ~55 and ~70 Å were observed and assigned to hemoglobin free membranes, in agreement with our findings. Large amounts of hemoglobin were reported to result in much larger lamellar periodicities of ~110 Å [67]. The electron density in FIG. 5a) agrees qualitatively well with the early electron density in [68], which was assigned to intact, hemoglobin-free erythrocyte membranes.

Membrane Orientation

The orientation of the RBC membranes in the stack was determined from the 2-dimensional data in FIG. 5b) by radial integration using Hermans orientation function, as described in the Materials and Methods Section. The intensity of the first reflectivity peak as function of the meridional angle φ is plotted in FIG. 6c). The degree of orientation was determined to be 90.9% (±0.26%). While values of ~97% are reported for synthetic supported membranes [69], the value for the RBC membrane is to the best of our knowledge the highest ever reported for a biological membrane. This high degree of orientation of the RBC membrane on silicon chips is required for a detailed structural characterization of the membranes, in particular to differentiate in-plane and out-of-plane structure.

Determination of Domain Size

The in-plane diffraction signals in FIG. 5d) are significantly broader than typical Bragg peaks in crystalline materials, indicating that the corresponding phases are small. The domain sizes can be estimated from the peak widths of the corresponding correlation peaks using Scherrer's equation (as detailed in the Materials and Methods Section). Values for the domain size, ξ, are listed in Table 1. From these results, RBC membranes consist of small, nanometer sized domains of $l_o$ and $l_d$ lipids and coiled-coil α-helical peptides The Effect of Aspirin on RBC Membrane Structure There is growing evidence for an influence of various pharmaceuticals on lipid membrane organization and stability [70]. In particular, non-steroidal anti-inflammatory drugs (NSAID's) have been shown to disturb bilayer structures in native and model membranes [71, 72]. Aspirin is the most common NSAID and is known to interact with membranes [51, 71]. Aspirin strongly perturbs model membrane structure in a concentration dependent manner and influences human erythrocyte shape [73] and decreases the hydrophobic surface barrier in mucosal membranes, leading to a diffusion of acid and gastrointestinal injury [74] and impacts on protein sorting [75]. Aspirin was previously reported to partition into lipid bilayers and position itself in the lipid head group region [24, 51, 76]. Recently, an interaction between aspirin and cholesterol was reported, as aspirin was observed to reduce the volume of cholesterol plaques in model membranes at elevated cholesterol concentrations of ~40 mol % [76]. Aspirin also inhibits the formation of cholesterol rafts in fluid lipid membranes at physiological cholesterol concentrations [24, 76].

In this section it is disclosed that: Aspirin partitions in RBC membranes, preferably in $l_o$ lipid domains, and is located in the membrane head group region. Aspirin also reduces membrane thickness and increases lipid tail distances, indicative of a fluidification of the RBC membranes.

The out-of-plane scattering for RBC membranes containing 1 mM, 1.5 mM, 2 mM, 2.5 mM and 3 mM ASA is shown in FIG. 7a). The curve containing 2.5 mM ASA and the corresponding fit is shown in part b). Data is well fit by 3 series of Bragg peaks, corresponding to $l_o$, $l_d$ and peptide domains, in agreement with pure RBC membranes.

Electron density profiles of the $l_o$ lipid domain for RBC membranes and RBC membranes+1 mM aspirin are shown in FIG. 7c). Upon the addition of aspirin, the electron density increases at z~22.8 Å. Under the assumption that a small amount of aspirin does not disturb the bilayer structure significantly, the two densities can be subtracted and the extra intensity assigned to aspirin molecules. The experiments thus locate aspirin inside the head group region of the RBC membranes, in agreement with results in model phospholipid bilayers [24, 51, 76]. There is only a small effect of aspirin on the electron density of the $l_d$ domains, as shown in FIG. 7e), indicating that aspirin preferably interacts with $l_o$ regions.

The lamellar spacing, $d_z$ and head group to head group spacing, $d_{HH}$, of the $l_o$ and ld lipid domains as function of ASA content are depicted in FIG. 7d). While lamellar spacing and membrane thickness for the $l_d$ lipid domains are not affected by the presence of ASA, the two spacings significantly decrease with increasing aspirin concentrations for the $l_o$ lipid domains. They decrease until lamellar spacing and membrane thickness for $l_o$ and ld domains coincide at a ASA concentration of 2.5 mM. At this ASA concentration, the overall lamellar spacing of the RBC membranes is reduced to 53.4 Å, the overall membrane thickness to 41.8 Å.

While the lipid spacing in the ld domain is unchanged by the presence of aspirin, the q∥-value of the lo signal slightly shifts to smaller q∥-values, indicative of an increase in the distance between lipids from $a_{lo}$=4.69 Å to $a_{lo}$=4.85 Å, and an increase in tail area from 19.04 Å$^2$ to 20.37 Å$^2$. Lipid domain sizes are approximately independent of aspirin concentration, however, a slight increase in peptide domain size was observed with increasing ASA content. A cartoon of the structure of RBC membranes in the presence of ASA is shown in FIG. 8b).

Conclusions

Presented here is the preparation of human red blood cell membranes on a chip, i.e. highly aligned multi-lamellar stacks of RBC membranes applied on silicon wafers. These solid supported RBC membranes are ideally suited for analysis using biophysical techniques and development of sensors for blood tests. Based on the protocol for the preparation of red blood cell ghosts, small uni-lamellar RBC vesicles were produced, which are applied onto functionalized silicon chips and annealed into multi-lamellar, planar membranes. Morphology and molecular structure of the RBC membranes were analyzed by optical microscopy, fluorescent microscopy, UV-vis spectroscopy and X-ray diffraction. These RBC's on a chip present a platform to test the interaction of bacteria and drugs with RBC membranes and determine their molecular mode-of-action in the future.

The X-ray diffraction measurements present direct experimental evidence that RBC membranes consist of nanometer sized $l_o$ and ld lipid domains, and α-helical coiled-coil peptide domains. The composition of RBC's was determined to be 30:45:25 ($l_o$:ld:coiled peptides).

RBC membranes that contain up to 3 mM of ASA were prepared. Presented here is experimental evidence that aspirin partitions in RBC membranes and preferably locates in the head groups region of the $l_o$ lipid domains. ASA led to an increase of the lipid-lipid distance and a decrease of the membranes thickness, indicative of a fluidification of the RBC membranes.

Example 2. Hemolysis Assay Based on a Human Red Blood Cell Membrane (HBLOC) Sensor Inventors have developed a method which isolates human red blood cells on a silicon chip for use as a safe and quantitative test for hemolytic bacteria. To develop our human blood cells on a chip, a sample of human blood is exposed to a hypotonic solution which causes the RBC's to burst and empty their contents. A series of sonication and washing steps are then applied to isolate only the RBC membrane, and to remove all hemoglobin and other contaminants. The result is a solution of empty membrane sacks known as RBC "ghosts". This solution is then applied to sensors and allowed to slowly dry, leaving behind stacked sheets of RBC membrane. The sensors use nanostructured gold electrodes, functionalized for the application of the RBC membranes and maximizing the surface area for increased sensitivity of the tests. The coated electrodes are then used as part of a 3-electrode electrochemical cell, where any damage to the cell membrane allows a redox-indicator in solution to access the electrode surface. Under cyclic voltammetry or chronoamperometry measurements the reduction/oxidation of the indicator molecule gives rise to a current that is proportional to the amount of membrane damage.

Nanostructured gold electrodes have been fabricated and the RBC membranes successfully applied to the sensors (FIG. 9). Membrane damage was quantitatively measured using ferricyanide as the redox indicator and cyclic voltammetry. To mimic hemolytic activity by bacteria attacking RBC membranes, the membranes were disrupted using a surfactant (sodium dodecyl sulfate, SDS). The voltammograms and bar graph show increases in the reduction and oxidation peak currents as a result of membrane damage and higher electroactive surface available (FIG. 10).

Example 3. RBC Ghost and Biosensor Preparation Protocol

Additional experiments were performed with respect to investigating the preparation of RBC ghosts from blood samples and the application of the RBC ghost preparations onto a substrate (silicon wafers) and to form multi-lamellar RBC membrane stacks.

The following protocol was observed to produce desirable preparations of RBC ghosts for annealing to form multi-lamellar RBC membrane stacks:
1. Take blood from volunteer.
2. Prepare Buffer:
   a. PBS Buffer: 2 Tablets of PBS in 400 ml Ultra Pure Water
   b. Diluted PBS Buffer: 16 ml of PBS Buffer filled to 500 ml; Adjust the pH to 8 using KOH.
3. Wash Blood: Centrifuge Blood at maximum settings for 10 minutes and remove the supernatant (Plasma). Fill the Tube with PBS buffer to ensure a total volume of ~10 ml. Repeat this washing step twice.
4. Prepare 24 Eppendorf tubes in an ice bucket.
5. Remove the supernatant from the Blood tube after the last Washing step.
6. Mix 50 µl of the RBC fraction with 1 ml of diluted PBS buffer in each of the 24 Eppendorf tubes.
7. Vortex the tubes.
8. Let the tubes sit for 30 minutes.
9. Centrifuge the tubes at maximal settings (~20 000×g) for 30 minutes.

10. Remove the supernatant. And refill the tubes with 1 ml diluted buffer solution.
11. Vortex the tubes.
12. Centrifuge the tubes at maximal settings (~20 000×g) for 15 minutes.
13. Repeat steps 10 to 12 until the solution is clear.
14. The Ghosts may be stored in the Fridge.
15. Centrifuge all Eppendorf s at maximal settings (~20 000×g) for 15 minutes.
16. Remove the supernatant and combine all Pellets in one Eppendorf. It might be convenient to first combine 2×12 tubes and then combine these pellets.
17. Centrifuge the sample at maximal settings (~20 000×g) for 15 minutes.
18. Remove or add diluted PBS buffer to ensure a total volume of 0.5 ml. This will result in a RBC membrane concentration of ~14 mg/ml.
19. Sonicate the sample: Place the sample in an ice bucket and insert the sonication tip. Set the instrument to 5 second pulses and 50 second breaks at 20% Intensity for 20 minutes.
The sample should look milky first but clear up during sonication.
20. Centrifuge the sample at maximal settings (~20 000×g) for 20 minutes.

The following protocol was observed to produce desirable substrates for promoting the formation of multi-lamellar RBC membrane stacks:
1. Silicon wafers placed in a Glass dish.
2. Fill in 5 ml Hydrogen Peroxide and 15 ml Sulfuric Acid (98%) ("Piranha Solution").
This step ensures the wafer surface is hydrophilic.
3. Let the wafers sit for min 20 Minutes.
4. The beaker does not need to be heated (room temperature works).

The following protocol was used for contacting the preparation of RBC ghosts with the prepared silicon substrate:
1. Heat the 3d orbital shaker and the metal plate to 37 degrees.
2. Set the Shaker speed to 7 and the tilt to 8.
3. Take the wafer out of the Piranha solution and rinse it ONLY with Water (no Methanol).
4. Dry the wafer with nitrogen gas.
5. Place the metal plate on the 3D orbital shaker.
6. Place the wafer on the metal plate.
7. Slowly apply 100 μl of the Ghost solution onto the wafer.
8. Place a plastic lid on top of the wafer and tilt the lid with a Qtip.
9. Wait until the wafers look well dried.

The following protocol was then used to incubate the RBC ghosts on the substrate to promote the formation of multi-lamellar RBC membrane stacks:
1. Place the wafers in a glass beaker with a saturated Potassium Sulfate solution.
2. Seal the beaker with a lid and parafilm.
3. Place the beaker in the incubator at 37 degrees Celsius.
4. Let the wafers sit for 3 days.

FIG. 11 shows images of a biosensor and multi-lamellar RBC membrane stack prepared according to the protocol of the present example. FIG. 12(a) shows a 2D x-ray image of a biosensor comprising a prepared according to the protocol of the present example. FIG. 12(b) shows the reflectivity Bragg peaks. The narrow peaks go up to an order of 5 which indicates a very well ordered and uniform membrane film.

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

|  | saturated lipid domains | unsaturated lipid domains | peptide domains |
|---|---|---|---|
| $d_z$ | 59.2 ± 0.5 Å | 51.6 ± 0.02 Å | 40.6 ± 0.06 Å |
| $d_{HH}$ | 46.0 ± 0.5 Å | 41.0 ± 0.02 Å | — |
| $d_w$ | 13.2 ± 0.5 Å | 10.6 ± 0.02 Å | — |
| a | 4.68 ± 0.27 Å | 5.39 ± 0.03 Å | 10.88 ± 0.22 Å |
| A | 19.04 ± 1.10 Å | 25.18 ± 0.13 Å | — |
| Ξ | 16 ± 3 Å | 29 ± 2 Å | 28 ± 3 Å |

REFERENCES

[1] James T Dodge, Carolyn Mitchell, and Donald J Hanahan, "The preparation and chemical characteristics of hemoglobin-free ghosts of human erythrocytes," Archives of biochemistry and biophysics 100, 119-130 (1963).
[2] G Schwoch and H Passow, "Preparation and properties of human erythrocyte ghosts," Molecular and cellular biochemistry 2, 197-218 (1973).
[3] Lars Kaestner, "Red blood cell ghosts and intact red blood cells as complementary models in photodynamic cell research," Bioelectrochemistry 62, 123-126 (2004).
[4] Theodore L Steck, "The organization of proteins in the human red blood cell membrane a review," The Journal of cell biology 62, 1-19 (1974).
[5] A. J Verkleij, R. F. A Zwaal, B Roelofsen, P Comfurius, D Kastelijn, and L. L. M van Deenen, "The asymmetric distribution of phospholipids in the human red cell membrane. a combined study using phospholipases and freeze-etch electron microscopy," Biochimica et Biophysica Acta (BBA)—Biomembranes 323, 178-193 (1973).
[6] Narla Mohandas and Patrick G Gallagher, "Red cell membrane: past, present, and future," Blood 112, 3939-3948 (2008).
[7] T. H. Watts, A. A. Brian, J. W. Kappler, P. Marrack, and H. M. McConnell, "Antigen presentation by supported planar membranes containing affinity-purified I-Ad," Proc. Natl. Acad. Sci. U.S.A. 81, 7564-7568 (1984).
[8] G. Pabst, N. Kučerka, M.-P. Nieh, M. C. Rheinstädter, and J. Katsaras, "Applications of neutron and x-ray scattering to the study of biologically relevant model membranes," Chemistry and Physics of Lipids 163, 460-479 (2010).
[9] Ilya Reviakine and Alain Brisson, "Formation of supported phospholipid bilayers from unilamellar vesicles investigated by atomic force microscopy," Langmuir 16, 1806-1815 (2000).
[10] John F. Nagle and Stephanie Tristram-Nagle, "Structure of lipid bilayers," Biochim. Biophys. Acta 1469, 159-195 (2000).
[11] S. H. Chen, C. Y. Liao, H. W. Huang, T. M. Weiss, M. C. Bellisent-Funel, and F. Sette, "Collective dynamics in fully hydrated phospholipid bilayers studied by inelastic x-ray scattering," Phys. Rev. Lett. 86, 740-743 (2001).

[12] M. C. Rheinstädter, C. Ollinger, G. Fragneto, F. Demmel, and T. Salditt, "Collective dynamics of lipid membranes studied by inelastic neutron scattering," Phys. Rev. Lett. 93, 108107 (2004).

[13] M. Tanaka and E. Sackmann, "Polymer-supported membranes as models of the cell surface," Nature 437, 656-663 (2005).

[14] J Daillant, E Bellet-Amalric, A Braslau, T Charitat, G Fragneto, F Graner, S Mora, F Rieutord, and B Stidder, "Structure and fluctuations of a single floating lipid bilayer," Proceedings of the National Academy of Sciences of the United States of America 102, 11639-11644 (2005).

[15] Maikel C. Rheinstädter, Wolfgang Häussler, and Tim Salditt, "Dispersion relation of lipid membrane shape fluctuations by neutron spin-echo spectrometry," Phys. Rev. Lett. 97, 048103 (2006).

[16] Xinjian Zhou, Jose M Moran-Mirabal, Harold G Craighead, and Paul L McEuen, "Supported lipid bilayer/carbon nanotube hybrids," Nature nanotechnology 2, 185-190 (2007).

[17] Norbert Kučerka, Mu-Ping Nieh, and John Katsaras, "Fluid phase lipid areas and bilayer thicknesses of commonly used phosphatidylcholines as a function of temperature," Biochimica et Biophysica Acta (BBA)—Biomembranes 1808, 2761-2771 (2011).

[18] Maikel C Rheinstädter, "Lipid membrane dynamics," in Dynamics of Soft Matter: Neutron Applications, edited by Sow-Hsin Chen Victoria Garcia Sakai, Christiane Alba-Simionesco (Springer Science & Business Media, 2011) p. 263.

[19] Bradley Moores, Elizabeth Drolle, Simon J Attwood, Janet Simons, and Zoya Leonenko, "Effect of surfaces on amyloid fibril formation," PLoS One 6, e25954 (2011).

[20] Maikel Rheinstädter, Laura Toppozini, and Hannah Dies, "The interaction of bio-molecules with lipid membranes studied by x-ray diffraction," Zeitschrift für Physikalische Chemie 228, 1105-1120 (2014).

[21] Maikel C Rheinstädter, "Basic aspects and applications of lipids and protein dynamics," in Liposomes, Lipid Bilayers and Model Membranes: from Basic Research to Application, edited by Mu-Ping Nieh Norbert Kučerka, Georg Pabst and John Katsaras (CRC Press, 2014) pp. 111-124.

[22] Drew Marquardt, Richard J Alsop, Maikel C Rheinstädter, and Thad A Harroun, "Neutron scattering at the intersection of heart health science and biophysics," Journal of Cardiovascular Development and Disease 2, 125-140 (2015).

[23] Kelly Cathcart, Amit Patel, Hannah Dies, Maikel C Rheinstädter, and Cécile Fradin, "Effect of cholesterol on the structure of a five-component mitochondria-like phospholipid membrane," Membranes 5, 664-684 (2015).

[24] Richard J Alsop, Laura Toppozini, Drew Marquardt, Norbert Kučerka, Thad A Harroun, and Maikel C Rheinstädter, "Aspirin inhibits formation of cholesterol rafts in fluid lipid membranes," Biochimica et Biophysica Acta (BBA)-Biomembranes 1848, 805-812 (2015).

[25] Richard J Alsop, Clare L Armstrong, Amna Maqbool, Laura Toppozini, Hannah Dies, and Maikel C Rheinstädter, "Cholesterol expels ibuprofen from the hydrophobic membrane core and stabilizes lamellar phases in lipid membranes containing ibuprofen," Soft matter 11, 4756-4767 (2015).

[26] Jennifer Tang, Richard J Alsop, Matilda Backholm, Hannah Dies, An-Chang Shi, and Maikel C Rheinstädter, "Amyloid-f3 25-35 peptides aggregate into cross-f3 sheets in unsaturated anionic lipid membranes at high peptide concentrations," Soft matter 12, 3165-3176 (2016).

[27] Richard J Alsop, Adree Khondker, Jochen S Hub, and Maikel C Rheinstädter, "The lipid bilayer provides a site for cortisone crystallization at high cortisone concentrations," Scientific reports 6, 1-10 (2016).

[28] J Yang, L K Tamm, T W Tillack, and Z Shao, "New approach for atomic force microscopy of membrane proteins. the imaging of cholera toxin," Journal of molecular biology 229, 286-90 (1993).

[29] S A Jewell, R W Titball, J Huyet, C E Naylor, A K Basak, P Gologan, C P Winlove, and P G Petrov, "*Clostridium perfringens* α-toxin interaction with red cells and model membranes," Soft matter 11, 7748-61 (2015).

[30] K. Simons and E. Ikonen, "Functional rafts in cell membranes," Nature 387, 569572 (1997).

[31] Ka Simons and Mathias J. Gerl, "Revitalizing membrane rafts: new tools and insights," Nat Rev Mol Cell Biol 11, 688-699 (2010).

[32] Clare L. Armstrong, Drew Marquardt, Hannah Dies, Norbert Kučerka, Zahra Yamani, Thad A. Harroun, John Katsaras, An-Chang Shi, and Maikel C. Rheinstädter, "The observation of highly ordered domains in membranes with cholesterol," PLOS ONE 8, e66162 (2013).

[33] Sebastian Meinhardt, Richard L. C. Vink, and Friederike Schmid, "Monolayer curvature stabilizes nanoscale raft domains in mixed lipid bilayers," Proc. Natl. Acad. Sci. U.S.A. 110, 4476-4481 (2013).

[34] Maikel C. Rheinstädter and Ole G. Mouritsen, "Small-scale structures in fluid cholesterol-lipid bilayers," Curr. Opin. Colloid Interface Sci. 18, 440-447 (2013).

[35] Laura Toppozini, Sebastian Meinhardt, Clare L Armstrong, Zahra Yamani, Norbert Kučerka, Friederike Schmid, and Maikel C Rheinstädter, "Structure of cholesterol in lipid rafts," Physical review letters 113, 228101 (2014).

[36] Maikel C. Rheinstädter Richard J. Alsop, "Lipid rafts in binary lipid/cholesterol bilayers," in Membrane organization and lipid rafts in the cell and artificial membranes, Cell Biology Research Progress, edited by Angel Catala (Nova, 2016) pp. 17-42.

[37] Gerald J Roth, Nancy Stanford, and Philip W Majerus, "Acetylation of prostaglandin synthase by aspirin," Proc. Natl. Acad. Sci. U.S.A. 72, 3073-3076 (1975).

[38] Carlo Patrono, Luis A Garc'ia Rodriguez, Raffaele Landolfi, and Colin Baigent, "Low-dose aspirin for the prevention of atherothrombosis," N. Engl. J. Med. 353, 2373-2383 (2005).

[39] Valerie B ODonnell, Robert C Murphy, and Steve P Watson, "Platelet lipidomics modern day perspective on lipid discovery and characterization in platelets," Circulation research 114, 1185-1203 (2014).

[40] Sanford J Shattil and Richard A Cooper, "Membrane microviscosity and human platelet function," Biochemistry (Mosc.) 15, 4832-4837 (1976).

[41] Pannuru Padmavathi, Vaddi Damodara Reddy, Paramahamsa Maturu, and Nallanchakravarthula Varadacharyulu, "Smoking-induced alterations in platelet membrane fluidity and $Na+/K+$-ATPase activity in chronic cigarette smokers," J Atheroscler Thromb 17, 619-627 (2010).

[42] Karine Gousset, Willem F Wolkers, Nelly M Tsvetkova, Ann E Oliver, Cara L Field, Naomi J Walker, John H Crowe, and Fern Tablin, "Evidence for a physiological role for membrane rafts in human platelets," J. Cell. Physiol. 190, 117-128 (2002).

[43] E Beutler, C West, and K G Blume, "The removal of leukocytes and platelets from whole blood," J Lab Clin Med 88, 328-333 (1976).

[44] Giampaolo Minetti, Stephane Egée, Daniel Morsdorf, Patrick Steffen, Asya Makhro, Cesare Achilli, Annarita Ciana, Jue Wang, Guillaume Bouyer, Ingolf Bernhardt, Christian Wagner, Serge Thomas, Anna Bogdanova, and Lars Kaestner, "Red cell investigations: Art and artefacts," Blood Reviews 27, 91-101 (2013).

[45] W. B. Grazer, "The red cell membrane and its cytoskeleton," Biochemical Journal 198, 1-8 (1981).

[46] D. Tortorella and E. London, "Method for efficient pelleting of small unilamellar model membrane vesicles," Analytical Biochemistry 217, 176-180 (1994).

[47] R. Richter, A. Mukhopadhyay, and A. Brisson, "Pathways of lipid vesicle deposition on solid surfaces: A combined QCM-D and AFM study," Biophys. J. 85, 3035-3047 (2003).

[48] Clare L. Armstrong, Martin D. Kaye, Michaela Zamponi, Eugene Mamontov, Madhusudan Tyagi, Timothy Jenkins, and Maikel C. Rheinstädter, "Diffusion in single solid supported lipid bilayers studied by quasi-elastic neutron scattering," Soft Matter 6, 5864-5867 (2010).

[49] M. Lucio, C. Nunes, D. Gaspar, K. Golebska, M. Wisniewski, J. L. F. C. Lima, G. Brezesinski, and S. Reis, "Effect of anti-inflammatory drugs in phosphatidylcholine membranes: A fluorescence and calorimetric study," Chemical Physics Letters 471, 300-309 (2009).

[50] Stephanie Tristram-Nagle, Yufeng Liu, Justin Legleiter, and John F. Nagle, "Structure of gel phase dmpc determined by x-ray diffraction," Biophysical Journal 83, 3324-3335 (2002).

[51] Matthew A. Barrett, Songbo Zheng, Golnaz Roshankar, Richard J. Alsop, Randy K. R. Belanger, Chris Huynh, Norbert Kučerka, and Maikel C. Rheinstädter, "Interaction of aspirin (acetylsalicylic acid) with lipid membranes," PLoS ONE 7, e34357 (2012).

[52] Norbert Kučerka, Yufeng Liu, Nanjun Chu, Horia I. Petrache, Stephanie Tristram-Nagle, and John F. Nagle, "Structure of fully hydrated fluid phase DMPC and DLPC lipid bilayers using x-ray scattering from oriented multilamellar arrays and from unilamellar vesicles," Biophys. J. 88, 2626-2637 (2005).

[53] H. Dies, L. Toppozini, and M. C. Rheinstädter, "The interaction between amyloid-β peptides and anionic lipid membranes containing cholesterol and melatonin," PLOS ONE, 1-17 (2014).

[54] M. C. Rheinstädter, C. Ollinger, G. Fragneto, F. Demmel, and T. Salditt, "Collective dynamics of lipid membranes studied by inelastic neutron scattering," Phys. Rev. Lett. 93, 108107 (2004).

[55] R. Welti, D. A. Rintoul, F. Goodsaid-Zalduondo, S. Felder, and D. F. Silbert, "Gel-phase phospholipid in the plasma membrane of sterol-depleted mouse 1 m cells," The Journal of Biological Chemistry 256, 7528-7535 (1981).

[56] Danny Poinapen, Laura Toppozini, Hannah Dies, Daniel C W Brown, and Maikel C Rheinstädter, "Static magnetic fields enhance lipid order in native plant plasma membrane," Soft Matter 9, 6804-6813 (2013).

[57] J. Katsaras, V. A. Raghunathan, E. J. Dufourc, and J. Dufourcq, "Evidence for a two-dimensional molecular lattice in subgel phase DPPC bilayers," Biochemistry 34, 4684-4688 (1995).

[58] T. T. Mills, J. Huang, G. W. Feigenson, and J. F. Nagle, "Effects of cholesterol and unsaturated dopc lipid on chain packing of saturated gel-phase DPPC bilayers," Gen. Physiol. Biophys. 28, 126-139 (2009).

[59] Nicole Pinto, Fei-Chi Yang, Atsuko Negishi, Maikel C. Rheinstädter, Todd E. Gillis, and Douglas S. Fudge, "Self-assembly enhances the strength of fibers made from vimentin intermediate filament proteins," Biomacromolecules 15, 574-581 (2014).

[60] Fei-Chi Yang, Robert D. Peters, Hannah Dies, and Maikel C. Rheinstädter, "Hierarchical, self-similar structure in native squid pen," Soft Matter 10, 5541-5549 (2014).

[61] Fei-Chi Yang, Yuchen Zhang, and Maikel C Rheinstädter, "The structure of people's hair," PeerJ 2, e619 (2014).

[62] Yuchen Zhang, Richard J Alsop, Asfia Soomro, Fei-Chi Yang, and Maikel C Rheinstädter, "Effect of shampoo, conditioner and permanent waving on the molecular structure of human hair," PeerJ 3, e1296 (2015).

[63] Sébastien Neukirch, Alain Goriely, and Andrew C Hausrath, "Chirality of coiled coils: elasticity matters," Physical review letters 100, 038105 (2008).

[64] F H C Crick, "Is α-keratin a coiled coil?" Nature 170, 882-883 (1952).

[65] C Cohen and D A Parry, "α-helical coiled coils: more facts and better predictions," Science 263, 488-489 (1994).

[66] Andrei N Lupas and Markus Gruber, "The structure of α-helical coiled coils," Advances in protein chemistry 70, 37-38 (2005).

[67] S Knutton, J B Finean, R Coleman, and A R Limbrick, "Low-angle x-ray diffraction and electron-microscope studies of isolated erythrocyte membranes," Journal of cell science 7, 357-371 (1970).

[68] James B Stamatoff, Samuel Krimm, and Nancy Reid Harvie, "X-ray diffraction studies of human erythrocyte membrane structure," Proceedings of the National Academy of Sciences 72, 531-534 (1975).

[69] Richard J Alsop, Rafaëla Schober, and Maikel Christian Rheinstädter, "Swelling of phospholipid membranes by divalent metal ions depends on the location of the ions in the bilayers," Soft Matter (2016).

[70] M Lucio, J L F C Lima, and S Reis, "Drug-membrane interactions: significance for medicinal chemistry," Current medicinal chemistry 17, 1795-1809 (2010).

[71] Lenard M Lichtenberger, Yong Zhou, Vasanthi Jayaraman, Janice R Doyen, Roger G O'Neil, Elizabeth J Dial, David E Volk, David G Gorenstein, Mohan Babu Boggara, and Ramanan Krishnamoorti, "Insight into nsaid-induced membrane alterations, pathogenesis and therapeutics: characterization of interaction of nsaids with phosphatidylcholine," BBA-MOL CELL BIOL L 1821, 994-1002 (2012).

[72] Catarina Pereira-Leite, Claudia Nunes, and Salette Reis, "Interaction of nonsteroidal anti-inflammatory drugs with mem-branes: In vitro assessment and relevance for their biological actions," Progress in lipid research 52, 571-584 (2013).

[73] Mario Suwalsky, Jessica Belmar, Fernando Villena, Maria José Gallardo, Malgorzata Jemiola-Rzeminska, and Kazimierz Strzalka, "Acetylsalicylic acid (aspirin) and salicylic acid interaction with the human erythrocyte membrane bilayer induce in vitro changes in the morphology of erythrocytes," Archives of biochemistry and biophysics 539, 9-19 (2013).

[74] Lenard M Lichtenberger, Yong Zhou, Elizabeth J Dial, and Robert M Raphael, "Nsaid injury to the gastrointestinal tract: evidence that nsaids interact with phospholipids to weaken the hydrophobic surface barrier and induce the formation of unstable pores in membranes," J. Pharm. Pharmacol. 58, 1421-1428 (2006).

[75] Yong Zhou, Kwang-Jin Cho, Sarah J Plowman, and John F Hancock, "Nonsteroidal anti-inflammatory drugs alter the spatiotemporal organization of ras proteins on the plasma membrane," Journal of Biological Chemistry 287, 16586-16595 (2012).

[76] Richard J Alsop, Matthew A Barrett, Songbo Zheng, Hannah Dies, and Maikel C Rheinstädter, "Acetylsalicylic acid (asa) increases the solubility of cholesterol when incorporated in lipid membranes," Soft matter 10, 4275-4286 (2014).

[77] Photoelectric Spectrometry Group and Institut für Spektrochemie und Angewandte Spektroskopie, UV Atlas of Organic Compounds: UV Atlas Organischer Verbindungen, UV Atlas of Organic Compounds: UV Atlas Organischer Verbindungen No. Bd. 2 (Plenum Press, 1966).

[78] J. F. Nagle and M. C. Wiener, "Relations for lipid bilayers," Biophys. J. 55, 309-313 (1989).

[79] P. Scherrer, "Bestimmung der Größe und der inneren Struktur von Kollidteilchen mittels R"ontgenstrahlen," Göttinger Nachrichten Math. Phys. 2, 98-100 (1918).

The invention claimed is:

1. A biosensor comprising:
a solid substrate having a lipid bilayer compatible surface;
a multi-lamellar lipid membrane structure derived from a biological cell and localized on the lipid bilayer compatible surface, the multi-lamellar lipid membrane structure being prepared from red blood cells or red blood cell ghosts; and
an aqueous layer interposed between each lipid bilayer of the multi-lamellar lipid membrane structure.

2. The biosensor of claim 1, wherein the multi-lamellar lipid membrane structure comprises two stacked lipid bilayers.

3. The biosensor of claim 1, wherein the multi-lamellar lipid membrane structure is prepared by contacting the lipid bilayer compatible surface with a preparation of the red blood cell ghosts and incubating the lipid bilayer compatible surface with the preparation of the red blood cell ghosts at a temperature between about 30° C. and 60° C. and a relative humidity greater than 50%, wherein the red blood cell ghosts anneal to form the multi-lamellar lipid membrane structure.

4. The biosensor of claim 3, wherein the multi-lamellar lipid membrane structure is prepared by incubating the lipid bilayer compatible surface with the preparation of the red blood cell ghosts at a temperature between about 35° C. and 40° C. in the presence of a saturated potassium sulfate solution.

5. The biosensor of claim 1, wherein the solid substrate is a material selected from the group consisting of silicon dioxide ($SiO_2$), glass, polydimethylsiloxane (PDMS), polymethyl methacrylate (PMMA), and polycarbonate (PC).

6. The biosensor of claim 1, wherein the lipid bilayer compatible surface is hydrophilic.

7. The biosensor of claim 1, wherein the lipid bilayer compatible surface comprises acid treated $SiO_2$.

8. The biosensor of claim 1, wherein the biosensor comprises at least one electrode.

9. The biosensor of claim 8, wherein the at least one electrode comprises all or part of the lipid bilayer compatible surface.

10. The biosensor of claim 9, wherein the lipid bilayer compatible surface of the at least one electrode has been rendered hydrophilic.

11. The biosensor of claim 10, wherein the lipid bilayer compatible surface of the at least one electrode comprises a functionalized metal including functionalized gold.

12. The biosensor of claim 8, further comprising a power supply and/or a detector for detecting a change in current and/or potential.

13. The biosensor of claim 8, wherein the solid substrate comprises the at least one electrode and wherein the at least one electrode comprises a functionalized metal including gold, copper, silver, or platinum.

14. The biosensor of claim 1, wherein the biosensor comprises a microfluidic device, well, or channel for receiving a sample in fluid communication with the multi-lamellar lipid membrane structure.

15. A method of detecting membrane disruption activity in a sample, the method comprising:
a) contacting the sample with the biosensor of claim 1; and
b) detecting a change in the multi-lamellar lipid membrane structure in response to the sample.

16. The method of claim 15, wherein the biosensor comprises at least one electrode and detecting the change in the multi-lamellar lipid membrane structure comprises voltammetry, cyclic voltammetry, chronoamperometry, differential multi pulse voltammetry, double potential pulse techniques or additive differential pulse voltammetry.

17. The method of claim 15, wherein the sample in contact with the biosensor further comprises a redox-indicator.

18. The method of claim 15, wherein the sample is a biological sample from a subject, where the biological sample includes a blood sample or a tissue sample.

19. The method of claim 15, further comprising comparing the change detected in the multi-lamellar lipid membrane structure to a control.

20. The method of claim 19, wherein the control is representative of a change in the multi-lamellar lipid membrane structure in response to a hemolytic agent, and a similarity between the change detected in response to the sample and the control is indicative of the presence of a hemolytic agent in the sample.

21. The method of claim 20, wherein the hemolytic agent is a hemolytic bacteria.

22. A biosensor comprising:
a solid substrate having a lipid bilayer compatible surface;
a multi-lamellar lipid membrane structure derived from a biological cell and localized on the lipid bilayer compatible surface;
an aqueous layer interposed between each lipid bilayer of the multi-lamellar lipid membrane structure; and
at least one electrode.

* * * * *